(12) United States Patent
Barnes et al.

(10) Patent No.: US 12,005,856 B2
(45) Date of Patent: Jun. 11, 2024

(54) ELECTRONIC HARNESS CHECK SYSTEM

(71) Applicant: Indiana Mills & Manufacturing, Inc., Westfield, IN (US)

(72) Inventors: Amie Barnes, Kempton, IN (US); Norman Taylor, Tarpon Springs, FL (US); Brian Nelson Coffman, Gurley, AL (US); Shirish Vatkar, Noblesville, IN (US)

(73) Assignee: Indiana Mills & Manufacturing, Inc., Westfield, IN (US)

( * ) Notice: Subject to any disclaimer, the term of this patent is extended or adjusted under 35 U.S.C. 154(b) by 211 days.

(21) Appl. No.: 17/649,137

(22) Filed: Jan. 27, 2022

(65) Prior Publication Data

US 2022/0234540 A1 Jul. 28, 2022

Related U.S. Application Data

(60) Provisional application No. 63/199,815, filed on Jan. 27, 2021.

(51) Int. Cl.
*B60N 2/20* (2006.01)
*A61B 5/00* (2006.01)
(Continued)

(52) U.S. Cl.
CPC .......... *B60R 22/48* (2013.01); *A61B 5/6891* (2013.01); *B60N 2/2803* (2013.01);
(Continued)

(58) Field of Classification Search
CPC .... B60N 2/2851; B60N 2/2803; B60N 2/265; B60N 2/272; B60N 2/002;
(Continued)

(56) References Cited

U.S. PATENT DOCUMENTS 8,190,332 B2   5/2012  Saban
9,187,013 B2*  11/2015 Helm ................... B60N 2/2812
(Continued)

FOREIGN PATENT DOCUMENTS

CN   208585129 U   3/2019
CN   110742590 A   2/2020
(Continued)

OTHER PUBLICATIONS

PCT, Int. App. No. PCT/US2022/070382 International Search Report, 3 pages, dated May 18, 2022.
(Continued)

*Primary Examiner* — Syed A Islam
(74) *Attorney, Agent, or Firm* — Woodard, Emhardt, Henry, Reeves & Wagner, LLP

(57) ABSTRACT

A seat monitoring system including one or more shoulder belt tension sensors and one or more buckle belt tension seniors configured to monitor the tension in a harness of a child safety seat. The seat monitoring system further includes a headrest position sensor for monitoring the position of a headrest. The seat monitoring system includes a motor for automatic tensioning of the shoulder belts and buckle belt. The seat monitoring system includes an I/O device for inputting child specifications. The I/O device includes a step-by-step guide for properly securing the child within the child safety seat.

28 Claims, 35 Drawing Sheets

(51) Int. Cl.
  *B60N 2/28* (2006.01)
  *B60R 22/44* (2006.01)
  *B60R 22/48* (2006.01)
  *G01B 7/30* (2006.01)
  *G01L 1/22* (2006.01)
  *G01L 5/10* (2020.01)
  *G01V 3/08* (2006.01)

(52) U.S. Cl.
  CPC ............ *B60N 2/2851* (2013.01); *B60R 22/44* (2013.01); *G01B 7/30* (2013.01); *G01L 1/22* (2013.01); *G01L 5/10* (2013.01); *G01V 3/08* (2013.01); *A61B 2503/06* (2013.01); *B60N 2002/2815* (2013.01); *B60R 2022/4473* (2013.01); *B60R 2022/4816* (2013.01); *B60R 2022/4841* (2013.01)

(58) Field of Classification Search
  CPC .... B60N 2002/2815; G01V 3/08; G01L 5/10; G01L 1/22; G01B 7/30; A61B 5/6891; B60R 22/48; B60R 22/44
  See application file for complete search history.

(56) References Cited

U.S. PATENT DOCUMENTS

| | | | |
|---|---|---|---|
| 9,266,535 | B2 | 2/2016 | Schoenberg |
| 9,457,716 | B2 * | 10/2016 | Westmoreland ......... B60Q 9/00 |
| 11,230,246 | B1 * | 1/2022 | Beach .................. B60W 40/08 |
| 2002/0024205 | A1 * | 2/2002 | Curtis ..................... B60R 22/00 280/733 |
| 2003/0090133 | A1 * | 5/2003 | Nathan .................. B60N 2/832 297/217.3 |
| 2006/0057900 | A1 | 3/2006 | Lawrence et al. |
| 2008/0246316 | A1 * | 10/2008 | Carine ................. B60N 2/2812 297/217.2 |
| 2010/0253498 | A1 | 10/2010 | Rork et al. |
| 2013/0201013 | A1 | 8/2013 | Schoenberg |
| 2014/0184404 | A1 | 7/2014 | Schoenberg et al. |
| 2014/0292503 | A1 | 10/2014 | Schoenberg |
| 2014/0354022 | A1 | 12/2014 | Szakelyhidi et al. |
| 2018/0043860 | A1 | 2/2018 | Bailliard et al. |
| 2019/0084513 | A1 * | 3/2019 | Yamamoto .............. B60R 22/46 |
| 2020/0058210 | A1 | 2/2020 | Williams et al. |
| 2020/0269807 | A1 | 8/2020 | Tardif |

FOREIGN PATENT DOCUMENTS

| | | |
|---|---|---|
| CN | 210212326 U | 3/2020 |
| WO | 2018158605 A1 | 9/2018 |
| WO | 2020088182 A1 | 5/2020 |
| WO | 2020134031 A1 | 7/2020 |

OTHER PUBLICATIONS

PCT, Int. App. No. PCT/US2022/070382 Written Opinion of International Search Authority, 6 pages, dated May 18, 2022.

* cited by examiner

ELECTRONIC HARNESS CHECK SYSTEM

CROSS REFERENCE TO RELATED APPLICATIONS

This application claims the benefit of U.S. patent application Ser. No. 63/199,815, filed Jan. 27, 2021, which is hereby incorporated by reference.

BACKGROUND

Child safety or car seats are designed to protect children when in a vehicle. Unfortunately, sometimes child car seats are used incorrectly. For example, the harness may be incorrectly tightened or the buckle of harness might not be properly engaged. This issue can be exacerbated when attempting to secure an unruly infant or child into the child car seat. Thus, there is a need for improvement in this field.

SUMMARY

A unique child seat monitoring system has been developed to address the above-mentioned as well as other issues. The child seat monitoring system includes sensors in communication with an input/output (I/O) device to assist a user in properly securing a child in a child safety seat. The child seat monitoring system includes a headrest position sensor, a seat occupancy sensor, one or more harness tension sensors, and a buckle sensor. The sensors communicate with a processor. The processor is in communication with the I/O device, such as a display, speaker, mobile device, and/or a series of light emitting diodes (LEDS) on the car seat. The headrest position sensor monitors the vertical position of an adjustable headrest in the child safety seat and assures the proper headrest height for a child or infant. The seat occupancy sensor determines whether a child is sitting in the seat or not. The harness tension sensors determine the harness tension, and the seat monitoring system compares the tension to a specified tension or tension range to ensure a child is properly secured. The buckle sensor determines if the child is properly buckled within the child safety seat. The I/O device gives a representation (e.g., visually and/or audibly) of the sensor readings to show a user if the child is properly secured. For example, the device may display a red X and/or other negative signal if the child is not properly secured.

To assist a user in properly securing a child within the seat, the seat includes a motor in communication with the processor and the harness tension sensors. The motor is configured to automatically tighten the harness once the child is buckled in the seat. For example, once the buckle sensor determines the child is properly buckled, the processor commands the motor to tighten the harness straps. As the straps tighten, the tension is monitored via the harness tension sensors. Once the harness tension reaches a predetermined value, the processor commands the motor to stop tensioning and the I/O device displays a checkmark or other positive signal showing the child is safely secured.

The system and techniques as described and illustrated herein concern a number of unique and inventive aspects. Some, but by no means all, of these unique aspects are summarized below.

Aspect 1 generally concerns a system that includes a child safety seat monitoring system.

Aspect 2 generally concerns the system of any previous aspect including a child safety seat.

Aspect 3 generally concerns the system of any previous aspect including a seat back.

Aspect 4 generally concerns the system of any previous aspect in which the child safety seat includes a seat back.

Aspect 5 generally concerns the system of any previous aspect including a headrest.

Aspect 6 generally concerns the system of any previous aspect in which the child safety seat includes a headrest.

Aspect 7 generally concerns the system of any previous aspect in which the headrest extends from the seat back.

Aspect 8 generally concerns the system of any previous aspect in which the headrest is configured to move relative to the seat back.

Aspect 9 generally concerns the system of any previous aspect including a seat bottom.

Aspect 10 generally concerns the system of any previous aspect in which the child safety seat includes a seat bottom.

Aspect 11 generally concerns the system of any previous aspect in which the seat bottom extends outward from the seat back.

Aspect 12 generally concerns the system of any previous aspect including a harness.

Aspect 13 generally concerns the system of any previous aspect in which the child safety seat includes a harness.

Aspect 14 generally concerns the system of any previous aspect in which the harness includes a buckle.

Aspect 15 generally concerns the system of any previous aspect in which the harness includes a chest clip.

Aspect 16 generally concerns the system of any previous aspect in which the harness includes one or more belts.

Aspect 17 generally concerns the system of any previous aspect in which the belts include a buckle belt.

Aspect 18 generally concerns the system of any previous aspect in which the buckle belt is coupled to the buckle.

Aspect 19 generally concerns the system of any previous aspect in which the buckle belt is coupled to the seat bottom.

Aspect 20 generally concerns the system of any previous aspect in which the belts include one or more shoulder belts.

Aspect 21 generally concerns the system of any previous aspect in which the shoulder belts extend from the seat back to the seat bottom.

Aspect 22 generally concerns the system of any previous aspect in which the harness includes a five-point harness.

Aspect 23 generally concerns the system of any previous aspect including a seat monitoring system.

Aspect 24 generally concerns the system of any previous aspect in which the seat monitoring system is configured to monitor status of a child safety seat.

Aspect 25 generally concerns the system of any previous aspect including an output device.

Aspect 26 generally concerns the system of any previous aspect in which the seat monitoring system includes an output device to provide the status of the child safety seat.

Aspect 27 generally concerns the system of any previous aspect in which the output device is configured to generate visual output.

Aspect 28 generally concerns the system of any previous aspect in which the output device includes a display.

Aspect 29 generally concerns the system of any previous aspect in which the display is mounted to the child safety seat.

Aspect 30 generally concerns the system of any previous aspect in which the output device includes one or more light emitting diodes (LEDs).

Aspect 31 generally concerns the system of any previous aspect in which the LEDs are integrated into the child safety seat.

Aspect 32 generally concerns the system of any previous aspect in which the output device includes a speaker.

Aspect 33 generally concerns the system of any previous aspect in which the output device is configured to generate sound.

Aspect 34 generally concerns the system of any previous aspect in which the output device is configured to generate tactile output.

Aspect 35 generally concerns the system of any previous aspect in which the output device is configured to vibrate.

Aspect 36 generally concerns the system of any previous aspect in which the output device includes an input/output (I/O) device.

Aspect 37 generally concerns the system of any previous aspect in which the I/O device includes a mobile device.

Aspect 38 generally concerns the system of any previous aspect including a processor.

Aspect 39 generally concerns the system of any previous aspect in which the seat monitoring system includes a processor.

Aspect 40 generally concerns the system of any previous aspect in which the processor is operatively coupled to the output device.

Aspect 41 generally concerns the system of any previous aspect in which the sensors.

Aspect 42 generally concerns the system of any previous aspect in which the seat monitoring system includes one or more sensors configured to sense the status of the child safety seat.

Aspect 43 generally concerns the system of any previous aspect in which the sensors operatively are coupled to the processor.

Aspect 44 generally concerns the system of any previous aspect in which the processor is operatively connected to the sensors.

Aspect 45 generally concerns the system of any previous aspect in which the processor is configured to monitor data from the sensors.

Aspect 46 generally concerns the system of any previous aspect in which the sensors include a headrest position sensor configured to determine position of the headrest of the child safety seat.

Aspect 47 generally concerns the system of any previous aspect in which the headrest position sensor includes a rotary sensor.

Aspect 48 generally concerns the system of any previous aspect in which the headrest position sensor includes a tape coupled to the headrest and the rotary sensor.

Aspect 49 generally concerns the system of any previous aspect in which the rotary sensor includes a spool.

Aspect 50 generally concerns the system of any previous aspect in which the tape is wrapped around the spool of the rotary sensor.

Aspect 51 generally concerns the system of any previous aspect in which the rotary sensor includes a digital rotary encoder.

Aspect 52 generally concerns the system of any previous aspect in which the digital rotary encoder includes an incremental type rotary encoder.

Aspect 53 generally concerns the system of any previous aspect in which the digital rotary encoder includes an absolute type rotary encoder.

Aspect 54 generally concerns the system of any previous aspect in which the rotary sensor includes a potentiometer.

Aspect 55 generally concerns the system of any previous aspect in which the length of the tape unspooled from the spool adjusts resistance of the potentiometer.

Aspect 56 generally concerns the system of any previous aspect in which the resistance of the potentiometer corresponds to the position of the headrest.

Aspect 57 generally concerns the system of any previous aspect in which the length of the tape unspooled from the spool corresponds to the position of the headrest.

Aspect 58 generally concerns the system of any previous aspect in which the raising the headrest extends a length of the tape extending from the rotary sensor.

Aspect 59 generally concerns the system of any previous aspect in which the lowering the headrest shortens the length of the tape extending from the rotary sensor.

Aspect 60 generally concerns the system of any previous aspect in which the headrest position sensor is configured to send headrest position information to the processor.

Aspect 61 generally concerns the system of any previous aspect in which the processor is configured to compare the headrest position to a specified position.

Aspect 62 generally concerns the system of any previous aspect in which the output device is configured to display a positive indicator when the position of the headrest matches the specified position.

Aspect 63 generally concerns the system of any previous aspect in which the output device is configured to display a negative indicator when the position of the headrest is different from a specified position.

Aspect 64 generally concerns the system of any previous aspect in which the processor is configured to determine the specified position for the headrest based on biometric information of an occupant of the child safety seat.

Aspect 65 generally concerns the system of any previous aspect in which the biometric information is inputted via the I/O device.

Aspect 66 generally concerns the system of any previous aspect in which the sensor includes an occupancy sensor configured to determine if an occupant is sitting in the child safety seat.

Aspect 67 generally concerns the system of any previous aspect in which the occupancy sensor is a pressure sensor.

Aspect 68 generally concerns the system of any previous aspect in which the occupancy sensor is located in the seat bottom.

Aspect 69 generally concerns the system of any previous aspect in which the sensors include a buckle sensor configured to sense buckling status of the buckle of the harness of the child safety seat.

Aspect 70 generally concerns the system of any previous aspect in which the output device is configured to provide an alert when the occupancy sensor determines an occupant is sitting on the child safety seat.

Aspect 71 generally concerns the system of any previous aspect in which the buckle sensor is operatively coupled to the processor.

Aspect 72 generally concerns the system of any previous aspect in which the output device is configured to provide an alert when the buckle sensor determines the buckle is properly buckled.

Aspect 73 generally concerns the system of any previous aspect in which the output device is configured to provide an alert when the buckle sensor determines the buckle is improperly buckled.

Aspect 74 generally concerns the system of any previous aspect in which the buckle sensor includes a reed switch.

Aspect 75 generally concerns the system of any previous aspect in which the sensors include one or more tension sensors configured to sense tension of the harness of the child safety seat.

Aspect 76 generally concerns the system of any previous aspect in which the tension sensors are operatively connected to the processor.

Aspect 77 generally concerns the system of any previous aspect in which the tension sensors include one or more shoulder belt tension sensors.

Aspect 78 generally concerns the system of any previous aspect in which the shoulder belt tension sensors are configured to measure tension of the shoulder belts of the harness.

Aspect 79 generally concerns the system of any previous aspect in which the shoulder belts are looped around the shoulder belt tension sensors.

Aspect 80 generally concerns the system of any previous aspect in which the tension sensors include a buckle belt tension sensor.

Aspect 81 generally concerns the system of any previous aspect in which the buckle tension sensor is configured to measure tension applied to the buckle belt of the harness of the child safety seat.

Aspect 82 generally concerns the system of any previous aspect in which the buckle tension sensor is operatively connected to the processor.

Aspect 83 generally concerns the system of any previous aspect in which the tension sensors include one or more strain gauges.

Aspect 84 generally concerns the system of any previous aspect in which the strain gauges are configured to sense buckling status of the buckle.

Aspect 85 generally concerns the system of any previous aspect in which the tension sensors are located in the seat bottom.

Aspect 86 generally concerns the system of any previous aspect in which the seat monitoring system is configured to automatically tighten the harness to a specified tension based on tension data from the tension sensors.

Aspect 87 generally concerns the system of any previous aspect in which the seat monitoring system is configured to automatically adjust tension of the harness based at least on tension data from the tension sensors.

Aspect 88 generally concerns the system of any previous aspect in which the seat monitoring system is configured to automatically tighten the harness.

Aspect 89 generally concerns the system of any previous aspect in which the seat monitoring system is configured to automatically loosen the harness.

Aspect 90 generally concerns the system of any previous aspect in which the seat monitoring system includes a motor configured to adjust the tension of the harness.

Aspect 91 generally concerns the system of any previous aspect in which the motor is operatively connected to the processor.

Aspect 92 generally concerns the system of any previous aspect in which the motor is configured to automatically tighten the harness based on commands from the processor.

Aspect 93 generally concerns the system of any previous aspect in which the motor is configured to automatically loosen the harness based on commands from the processor.

Aspect 94 generally concerns the system of any previous aspect in which the motor includes an electric motor.

Aspect 95 generally concerns the system of any previous aspect in which the output device is configured to provide a positive indicator when the harness reaches a safe tension.

Aspect 96 generally concerns the system of any previous aspect in which the output device is configured to provide a negative indicator when the harness is not at a safe tension.

Aspect 97 generally concerns the system of any previous aspect in which the motor is configured to tighten the harness when the buckle is buckled and the occupancy sensor detects an occupant.

Aspect 98 generally concerns the system of any previous aspect in which the motor is configured to loosen the harness when the buckle is unbuckled.

Aspect 99 generally concerns the system of any previous aspect in which the input device configured to receive user inputs concerning biometric information about the occupant of the child safety seat.

Aspect 100 generally concerns the system of any previous aspect in which the input device is integrated into the I/O device.

Aspect 101 generally concerns the system of any previous aspect in which the output device is configured to provide an alert when the headrest sensor determines the headrest is in a proper position.

Aspect 102 generally concerns the system of any previous aspect in which the output device is configured to provide an alert when the tension sensor determines the harness is properly tensioned.

Aspect 103 generally concerns the system of any previous aspect in which the seat monitoring system is integrated into the child safety seat.

Aspect 104 generally concerns the system of any previous aspect in which the child safety seat is an aftermarket product installed in a vehicle.

Aspect 105 generally concerns the system of any previous aspect in which the child safety seat is integrated into a vehicle seat by an original equipment manufacturer.

Aspect 106 generally concerns the system of any previous aspect in which the output device is configured to provide an indicator of the position of the headrest.

Aspect 107 generally concerns the method of operating the system of any previous aspect.

Aspect 108 generally concerns a system that operates according to the method of the previous aspect.

Aspect 109 generally concerns a method of operating a seat monitoring system.

Aspect 110 generally concerns a method of operating a child safety seat.

Aspect 111 generally concerns the method of any previous aspect including measuring a position of the headrest of the child safety seat with a headrest position sensor of a seat monitoring system.

Aspect 112 generally concerns the method of any previous aspect including determining with the seat monitoring system that the position of the headrest satisfies headrest specifications for the occupant.

Aspect 113 generally concerns the method of any previous aspect including determining that the child safety seat is occupied with an occupancy sensor of the seat monitoring system.

Aspect 114 generally concerns the method of any previous aspect including detecting buckling of a buckle of the harness with a buckle sensor of the seat monitoring system.

Aspect 115 generally concerns the method of any previous aspect including sensing tension of one or more belts of the harness with one or more tension sensors of the seat monitoring system.

Aspect 116 generally concerns the method of any previous aspect including tightening the belts of the harness until proper tension is reached.

Aspect 117 generally concerns the method of any previous aspect including detecting unbuckling of the buckle with the buckle sensor of the seat monitoring system.

Aspect 118 generally concerns the method of any previous aspect including loosening the belts of the harness in response to the detecting unbuckling.

Further forms, objects, features, aspects, benefits, advantages, and embodiments of the present invention will become apparent from a detailed description and drawings provided herewith.

DETAILED DESCRIPTION OF SELECTED EMBODIMENTS

Figure 1:
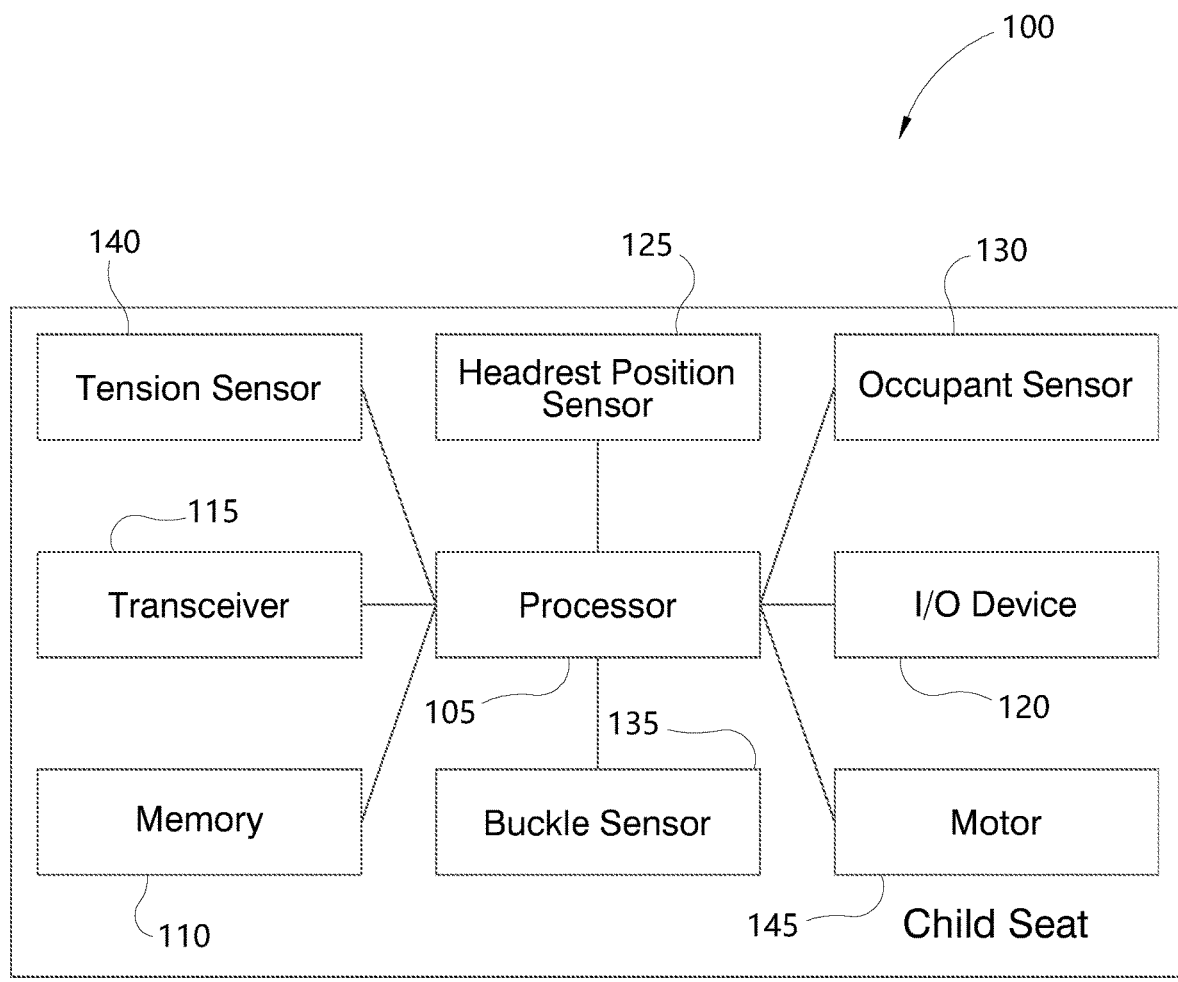
FIG. 1 is a diagrammatic view of a seat monitoring system.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments and any further applications of the principles of the invention as described herein are contemplated as would normally occur to one skilled in the art to which the invention relates. One embodiment of the invention is shown in great detail, although it will be apparent to those skilled in the relevant art that some features that are not relevant to the present invention may not be shown for the sake of clarity.

The reference numerals in the following description have been organized to aid the reader in quickly identifying the drawings where various components are first shown. In particular, the drawing in which an element first appears is typically indicated by the left-most digit(s) in the corresponding reference number. For example, an element identified by a "100" series reference numeral will likely first appear in FIG. 1, an element identified by a "200" series reference numeral will likely first appear in FIG. 2, and so on.

FIG. 1 shows an example of a seat monitoring system 100 configured to monitor and control a child safety seat. The seat monitoring system 100 uses visual, audible, tactile, and/or other indicators to step a user through a child or infant restraint process. The seat monitoring system 100 further monitors tension and headrest placement to ensure that a child is properly restrained within the seat. As should be appreciated, the seat monitoring system 100 enables parents to feel comfortable knowing that the child is safely restrained during car rides.

The seat monitoring system 100 includes a processor 105. The processor 105 is operatively connected to a memory 110, a transceiver 115, and an input/output device (I/O device) 120. In one example, I/O device 120 includes a series of light emitting diodes (LEDS). In another example, the I/O device 120 includes a mobile device such as a cell phone. In yet another example, the I/O device 120 is a display mounted adjacent the seat monitoring system 100. The I/O device 120 can further include speakers for generating sounds, alerts, and/or verbal instructions. The I/O device 120 in other variations can include a vibration or other tactile device. While the I/O device 120 will be described as having both input and output functions, separate output and input devices can be used. Moreover, when appropriate, the I/O device 120 can function solely as an output device or an input device.

The processor 105 is operatively connected to one or more headrest position sensors 125, one or more occupant sensors 130, one or more buckle sensors 135, and/or one or more tension sensors 140. In one example, the headrest position sensor 125 is a potentiometer configured to monitor headrest position. In another example, the occupant sensor 130 is a pressure sensor configured to determine whether or not a child is present in the seat monitoring system 100. In a further example, the buckle sensor 135 is a reed switch configured to determine whether or not a buckle is properly secured. In one embodiment, the tension sensor 140 is a load cell and/or strain gauge configured to determine the tension level of a restraint. The tension sensor 140 works in tandem with a motor 145. The motor 145 may tighten and/or loosen the restraints as required by the tension sensor 140. In one example, the motor 145 is an electric motor.

Figure 2:
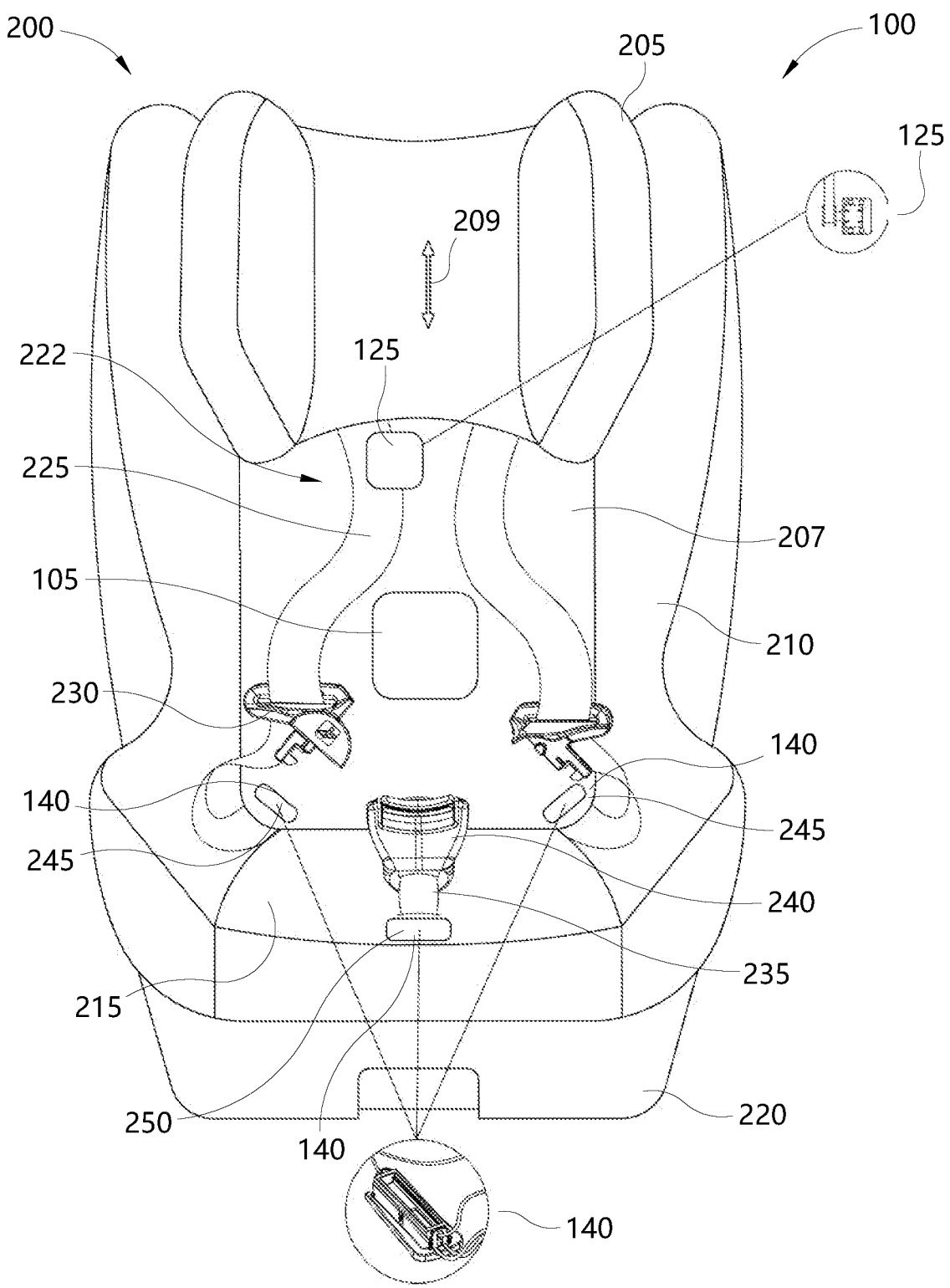
FIG. 2 is a front view of the FIG. 1 seat monitoring system incorporated in a child safety seat.

FIG. 2 depicts an example of the seat monitoring system 100 from FIG. 1 integrated into a child safety seat 200. In the illustrated example, the child safety seat 200 has a headrest 205, a seat back 207, a seat body 210, a seat bottom 215, and a seat base 220. Stored within the headrest 205 is a headrest position sensor 125. As depicted by arrow 209, the headrest 205 is able to move or be adjusted. The headrest position sensor 125 detects the movement of the headrest 205. For example, the headrest position sensor 125 is configured to determine the position of the headrest 205 and compare the position to a specified value or range. For example, a user may input a height and weight of a child into the I/O device 120 and the headrest position sensor 125 may indicate that the headrest 205 needs adjusted based on the specifications. In other examples, the headrest 205 may move vertically, horizontally, axially, and/or in other directions.

In the depicted example, the processor 105 is stored behind the seat back 207. The processor 105 is generally stored within the child safety seat 200 and may be accessible for maintenance/replacement via an access panel. The child safety seat 200 further includes a harness 222. The harness 222 includes one or more shoulder belts 225 extending along the seat back 207. The harness 222 is used to secure the child within the child safety seat 200. The shoulder belts 225 include one or more latch plates 230 to lock the shoulder belts 225 into position. The shoulder belts 225 may further include a chest clip to properly position the shoulder belts 225 and harness pads. The latch plates 230 may be designed to slide along the shoulder belts 225. Surrounding the seat back 207 is the seat body 210. The seat body 210 is configured to provide a comfortable and safe recessed area for the child. Located in the seat bottom 215 is a buckle belt 235. The buckle belt 235 includes a buckle 240 designed to interconnect with the latch plates 230 of the shoulder belts 225.

To assure proper tensioning of the shoulder belts 225, one or more shoulder belt tension sensors 245 are positioned to monitor the tension level. The shoulder belt tension sensors 245 are generally located behind the seat back 207 near the seat bottom 215. In one example, the shoulder belt tension sensors 245 work with the motor 145 to tighten the shoulder belts 225. Similarly, one or more buckle belt tension seniors 250 are positioned to monitor the tension level of the buckle belt 235. The buckle belt tension seniors 250 are generally located within the seat bottom 215.

The seat base 220 supports the seat bottom 215 and is configured to lock the child safety seat 200 into a vehicle. In one example, the seat base 220 locks the child safety seat 200 into the vehicle using a lower anchors and tethers for children (LATCH) or Isofix connectors.

Figure 3:
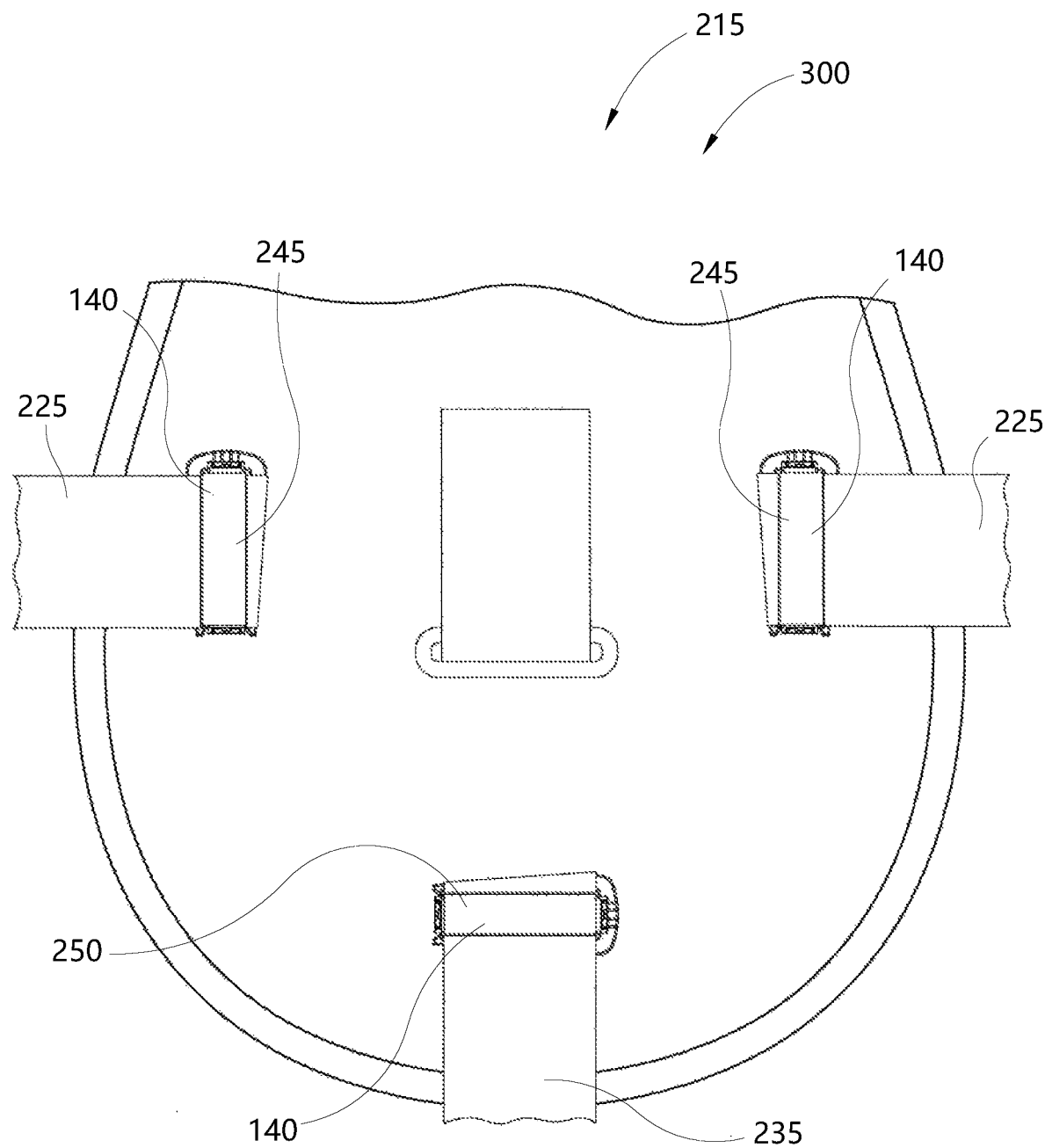
FIG. 3 is an interior view of a seat bottom from FIG. 2.
Figure 4:
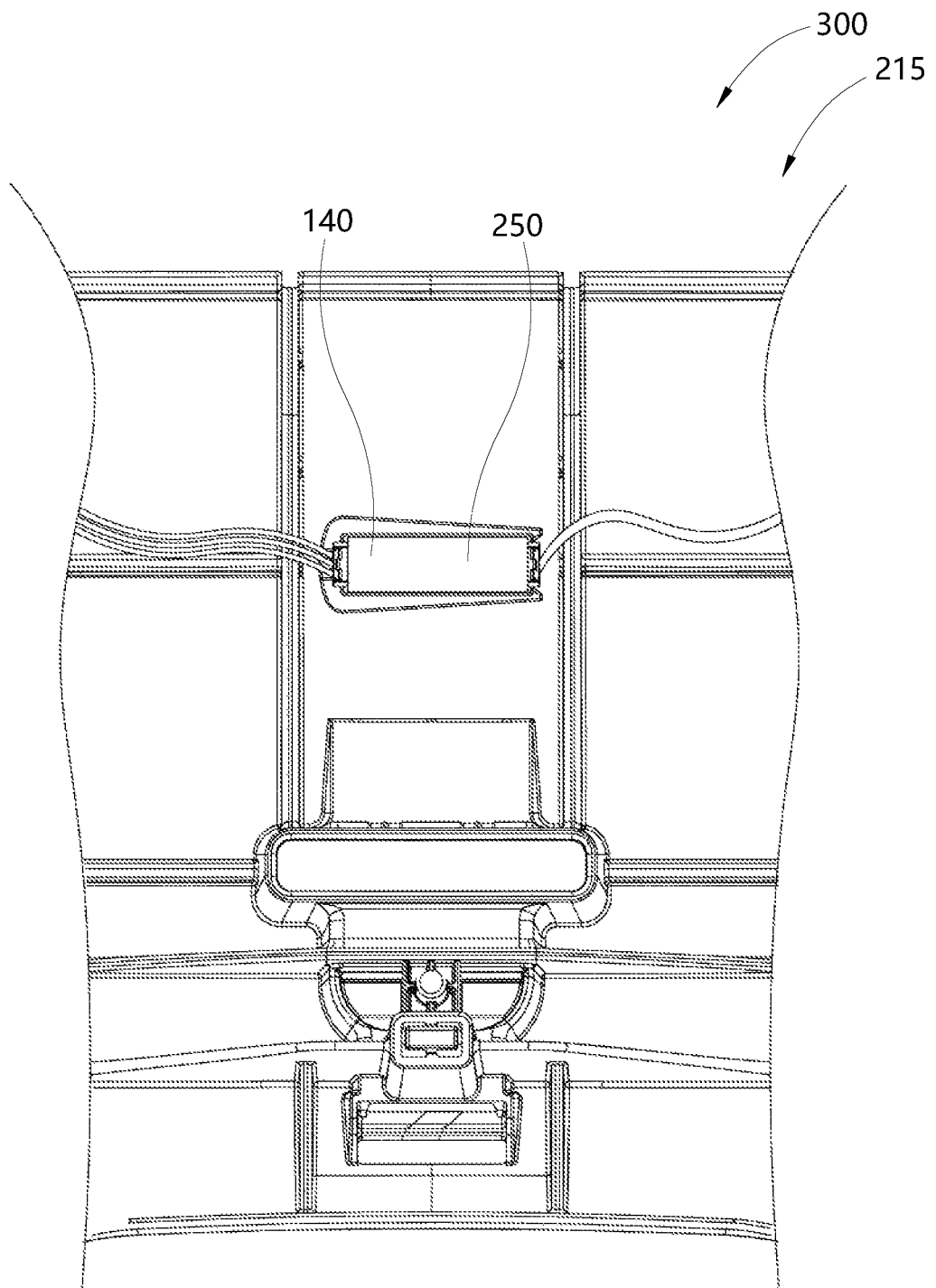
FIG. 4 is an interior view of the seat bottom of FIG. 2.

FIGS. 3 and 4 show an interior portion 300 of the seat bottom 215 of FIG. 2. The mounting locations of the shoulder belt tension sensors 245 are shown with respect to the shoulder belts 225. Similarly, the mounting location of the buckle belt tension sensor 250 is shown with respect to the buckle belt 235. Generally, the mounting locations are chosen to most accurately determine the amount of tension in the shoulder belts 225 and buckle belt 235. However, in other examples, the location of the shoulder belt tension sensors 245 and buckle belt tension sensor 250 may be different.

Figure 5:
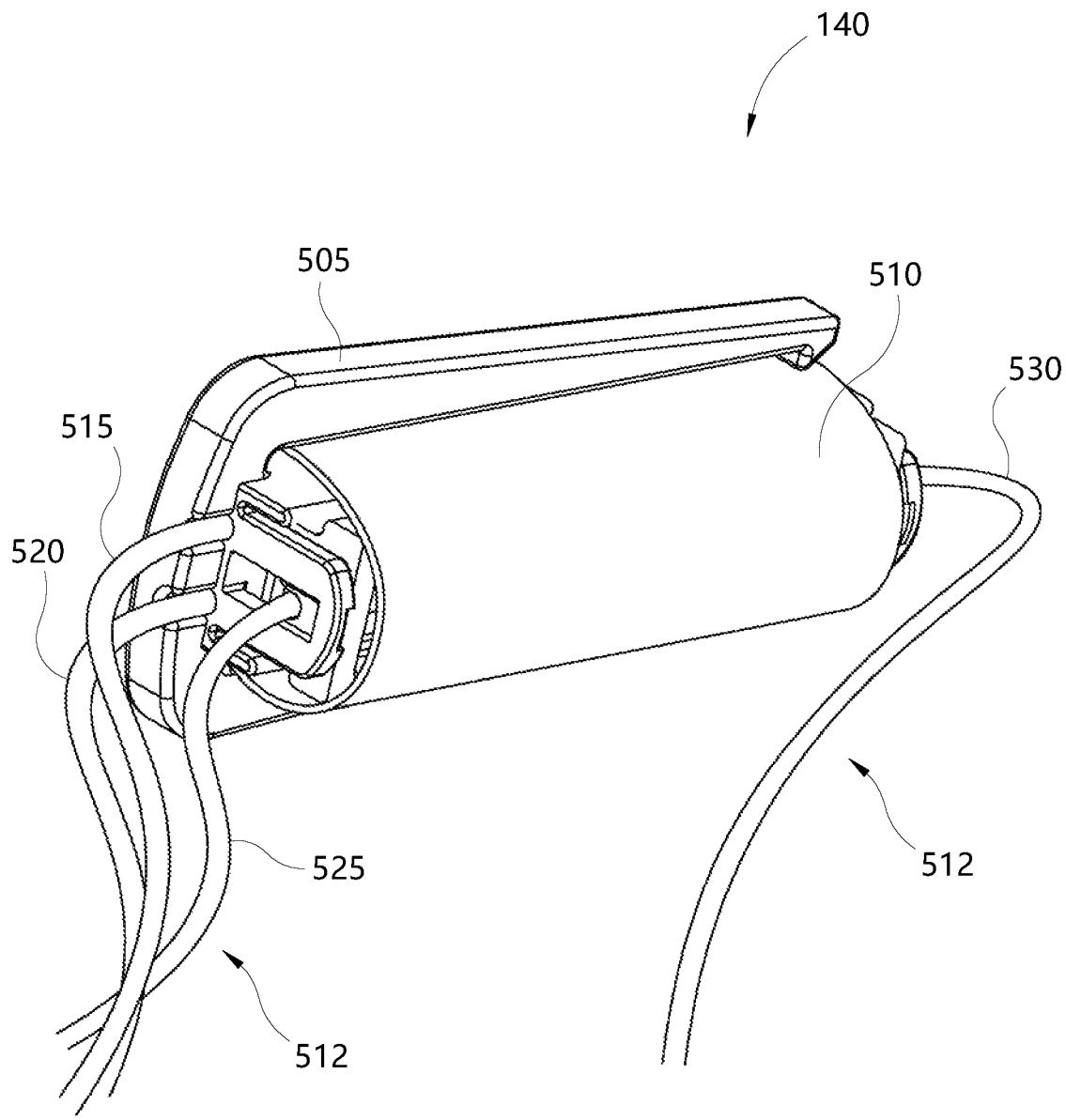
FIG. 5 is a perspective view of a tension sensor.
Figure 6:
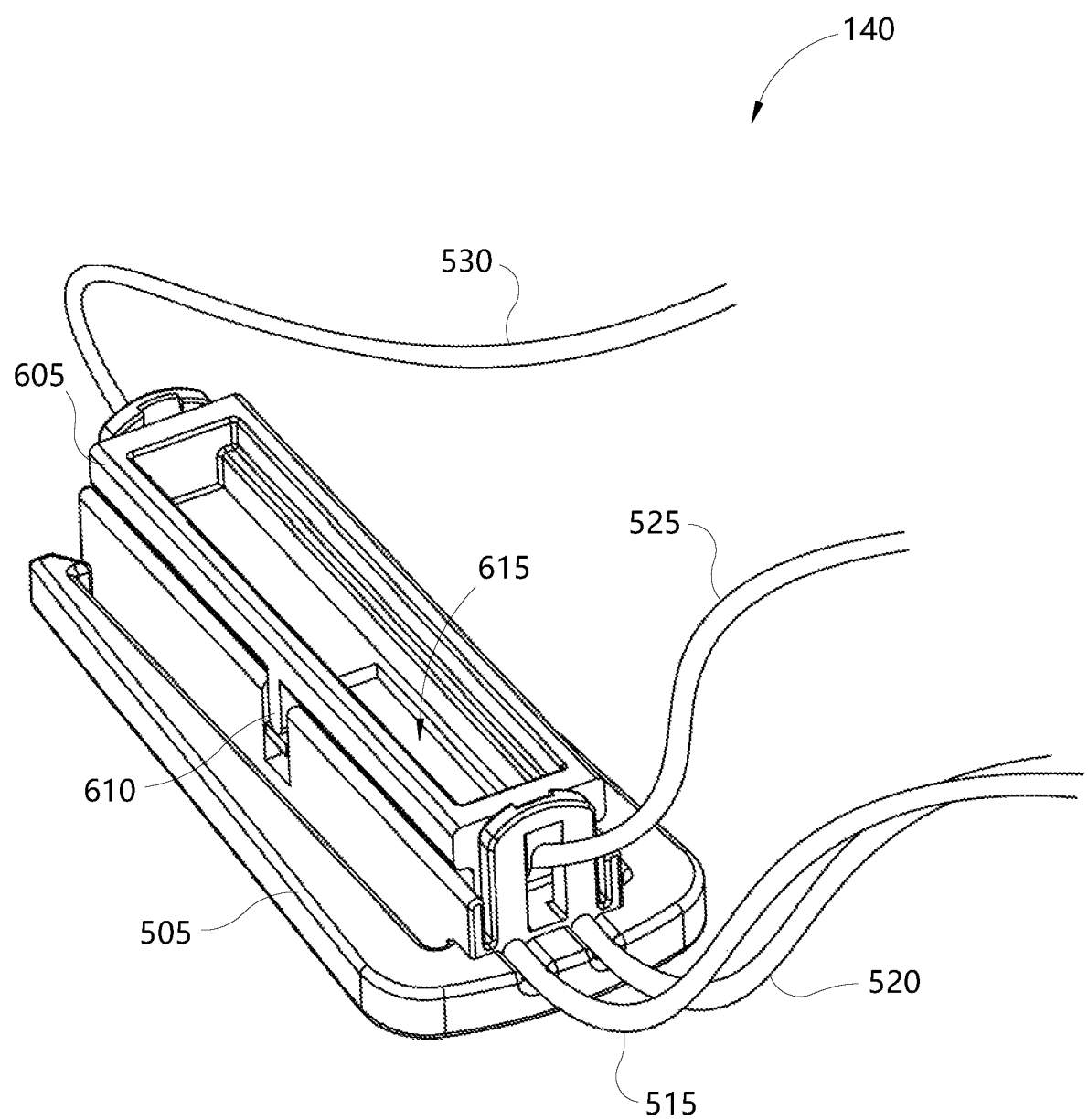
FIG. 6 is a perspective view of the tension sensor of FIG. 5 without a cover.
Figure 7:
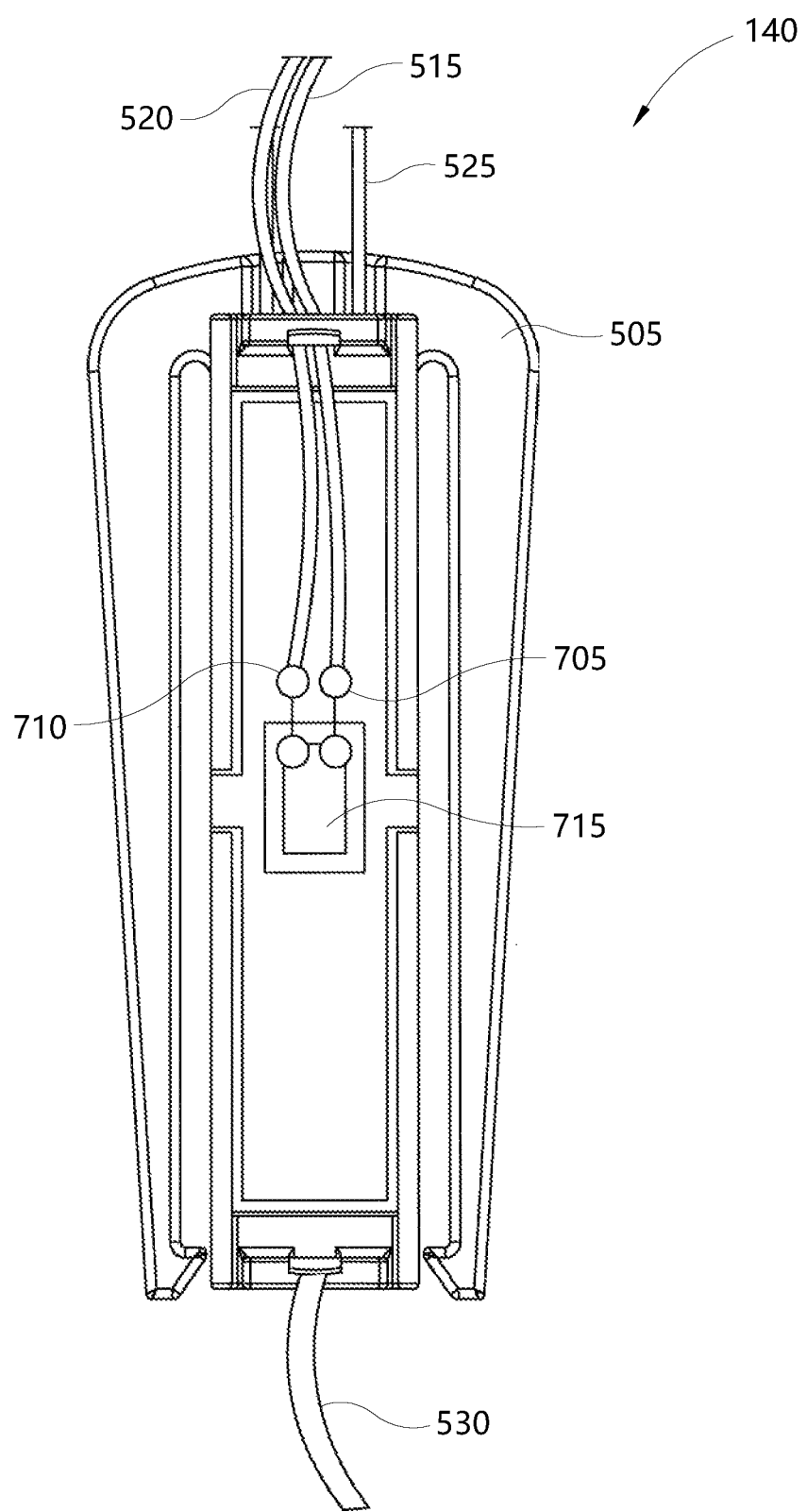
FIG. 7 is a top view of the tension sensor of FIG. 5 without the cover and actuator.

FIGS. 5, 6, and 7 show examples of the tension sensor 140 in various forms of disassembly. The tension sensor 140 is used to monitor the tension in the shoulder belts 225 and the buckle belt 235 to ensure that the harness 222 is not over tightened and/or too loose to secure the child properly. In one example, the tension sensor 140 may include a strain gauge. In another example, the tension sensor 140 may include a load cell.

The tension sensor 140 generally includes a base 505, a cover 510, and one or more wires 512. Generally, the wires 512 include a positive signal wire 515, a negative signal wire 520, a positive power wire 525, and a negative power wire 530. The positive signal wire 515 and negative signal wire 520 are configured to read a voltage differential. The voltage differential is the result of a force or load on the tension sensor 140. The tension sensor 140 then reads the force measurement as a voltage differential via the positive signal wire 515 and negative signal wire 520. The voltage differential is sent to the processor 105 where the digital reading is converted to a force measurement. The positive power wire 525 and negative power wire 530 serve as power sources/inputs for the tension sensor 140.

In FIG. 6, the cover 510 is removed to better show an actuator 605. The actuator 605 includes a plunger 610 configured to actuate a foil actuator 615. As shown best in FIG. 7, the foil actuator 615 deforms a foil 715. The deformation of the foil 715 modifies a resistance value of the foil 715, which in turn modifies a voltage measurement sensed by the positive signal wire 515 and negative signal wire 520. The positive signal wire 515 and negative signal wire 520 are connected to the foil 715 via a positive signal mounting location 705 and a negative signal mounting location 710.

Figure 8:
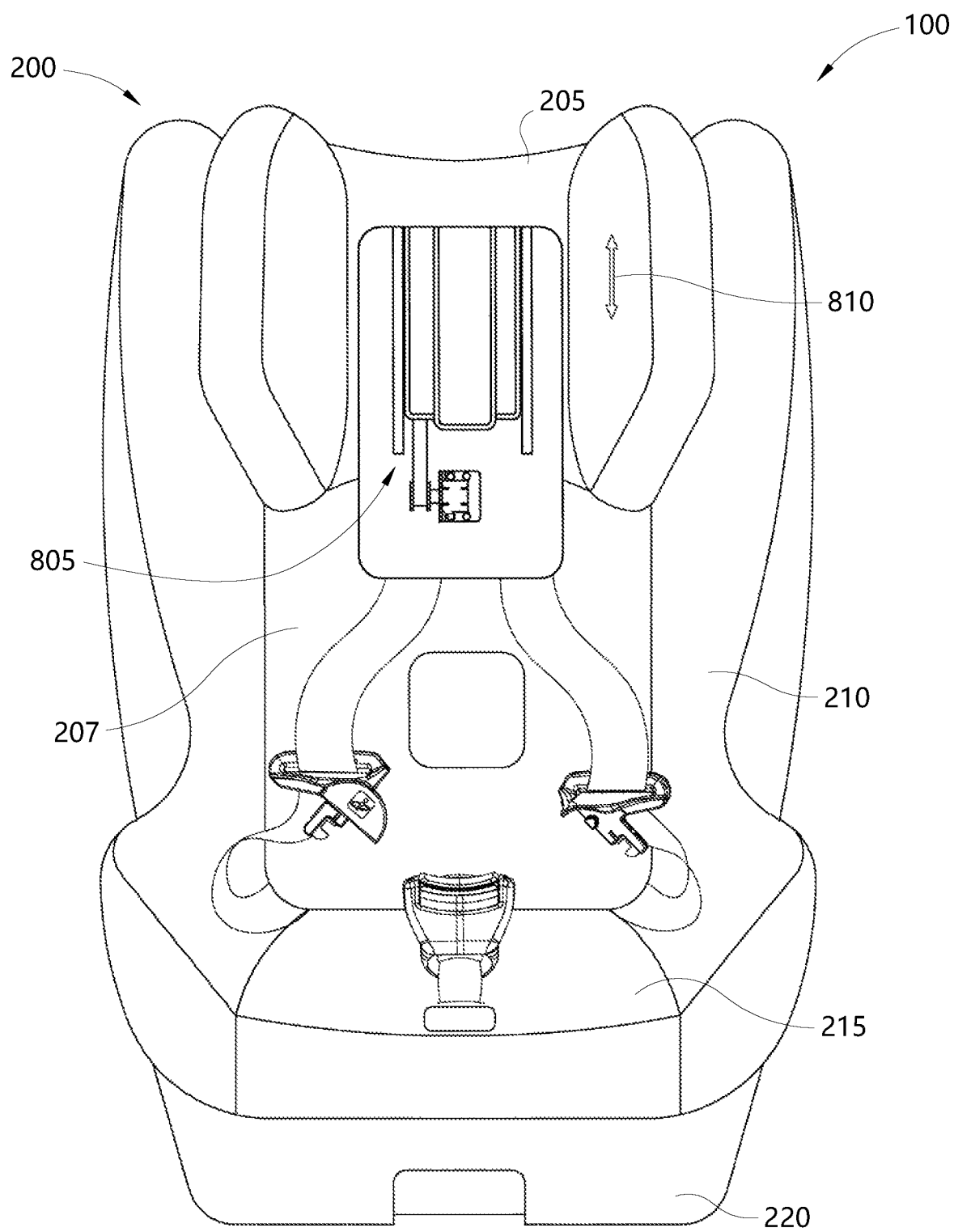
FIG. 8 is a front view of the seat monitoring system of FIG. 2 depicting a headrest sensor assembly.
Figure 9:
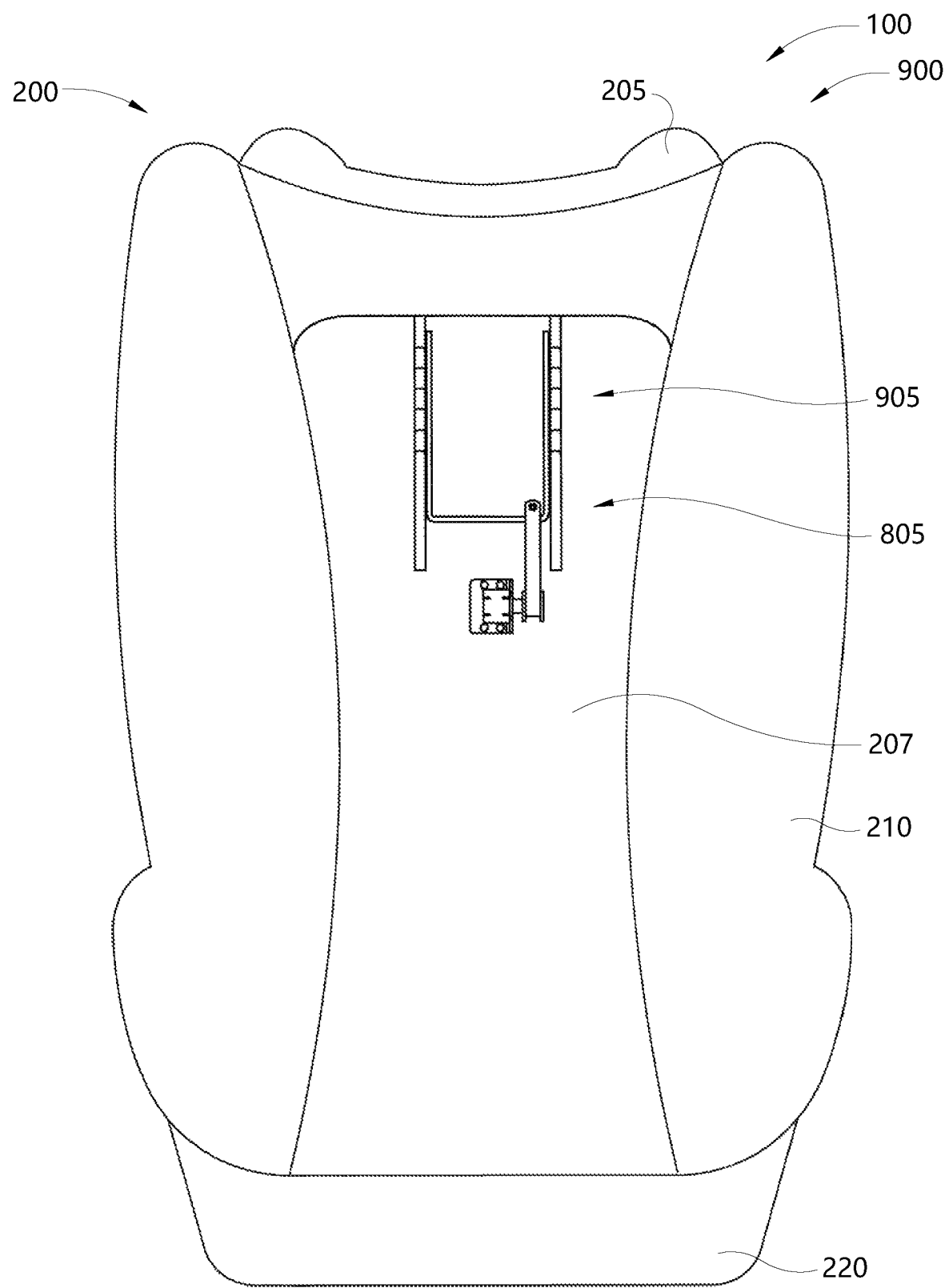
FIG. 9 is a rear view of the seat monitoring system of FIG. 8 depicting the headrest sensor assembly in a lowered position.
Figure 10:
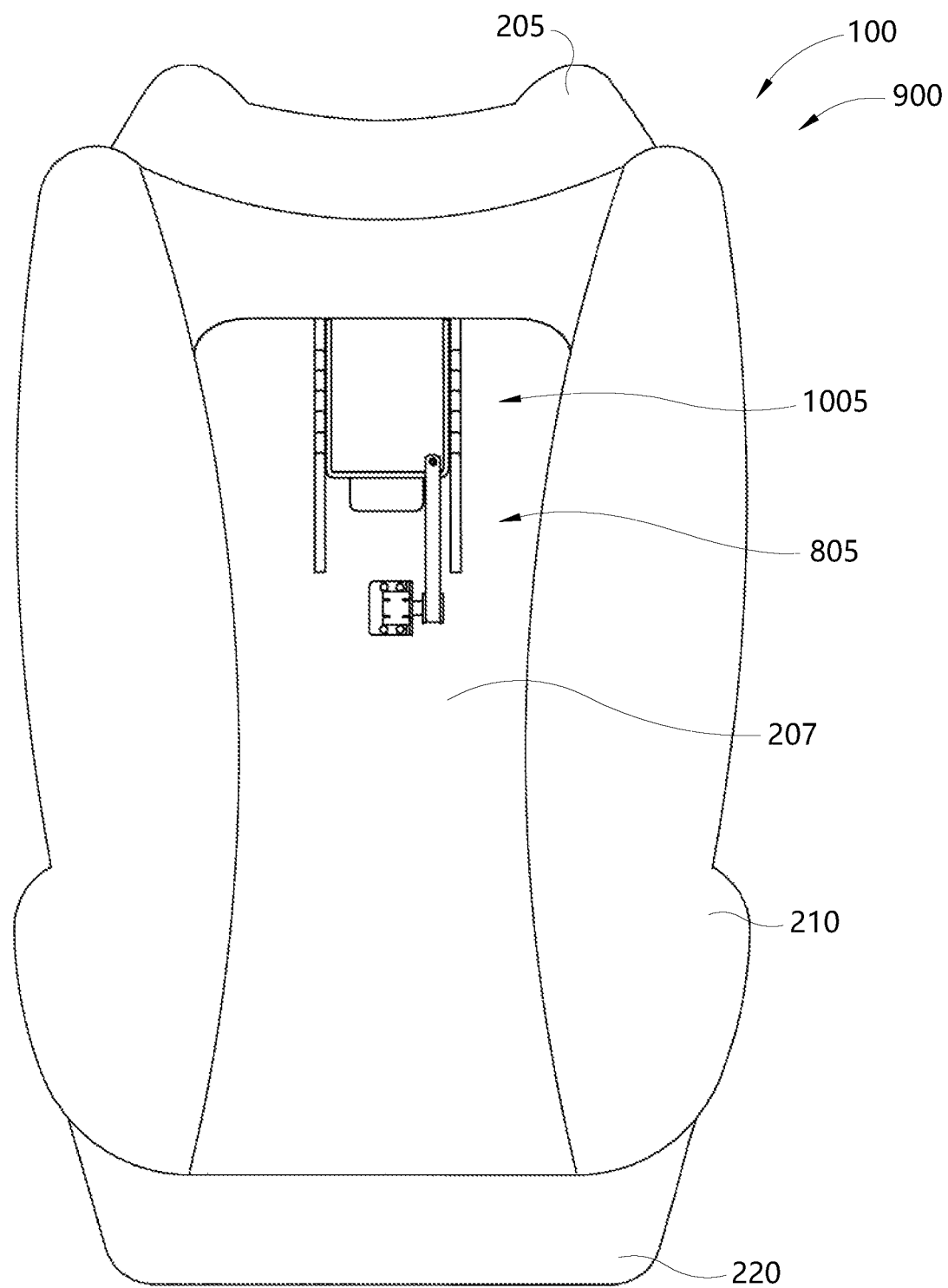
FIG. 10 is a rear view of the seat monitoring system of FIG. 8 depicting the headrest sensor assembly in a raised position.

Turning to FIGS. 8, 9, and 10, multiple examples of the child safety seat 200 depict an interior portion of the headrest 205 and seat back 207 in order to best show a headrest sensor assembly 805. The headrest sensor assembly 805 is configured to determine the position of the headrest 205 to confirm that the headrest 205 is in the correct position for a child. In one example, the headrest 205 is movable as indicated by arrow 810.

The headrest sensor assembly 805 is configured to determine the position of the headrest 205. In another example, the headrest sensor assembly 805 is configured to determine the position of the headrest 205 as well as an angled and/or rotational position of the headrest 205. In yet another example, the headrest sensor assembly 805 is configured to determine the position of the headrest 205 and send the position data to the processor 105 to determine if the position of the headrest 205 matches a specified position or a position range for the headrest 205. For example, the processor 105 may calculate a headrest 205 position based on a set of inputted child specifications, such as biometric information. The headrest sensor assembly 805 is generally positioned within the interior portion 300 of the headrest 205 and/or the seat back 207.

In FIG. 9, the seat monitoring system 100 is shown from a back side 900 with the headrest 205 in a lowered position 905. In FIG. 10 the seat monitoring system 100 is shown with the headrest 205 in a raised position 1005. As can be seen in FIGS. 9 and 10, the headrest sensor assembly 805 is mounted within the headrest 205 and the seat back 207 of the child safety seat 200.

Figure 11:
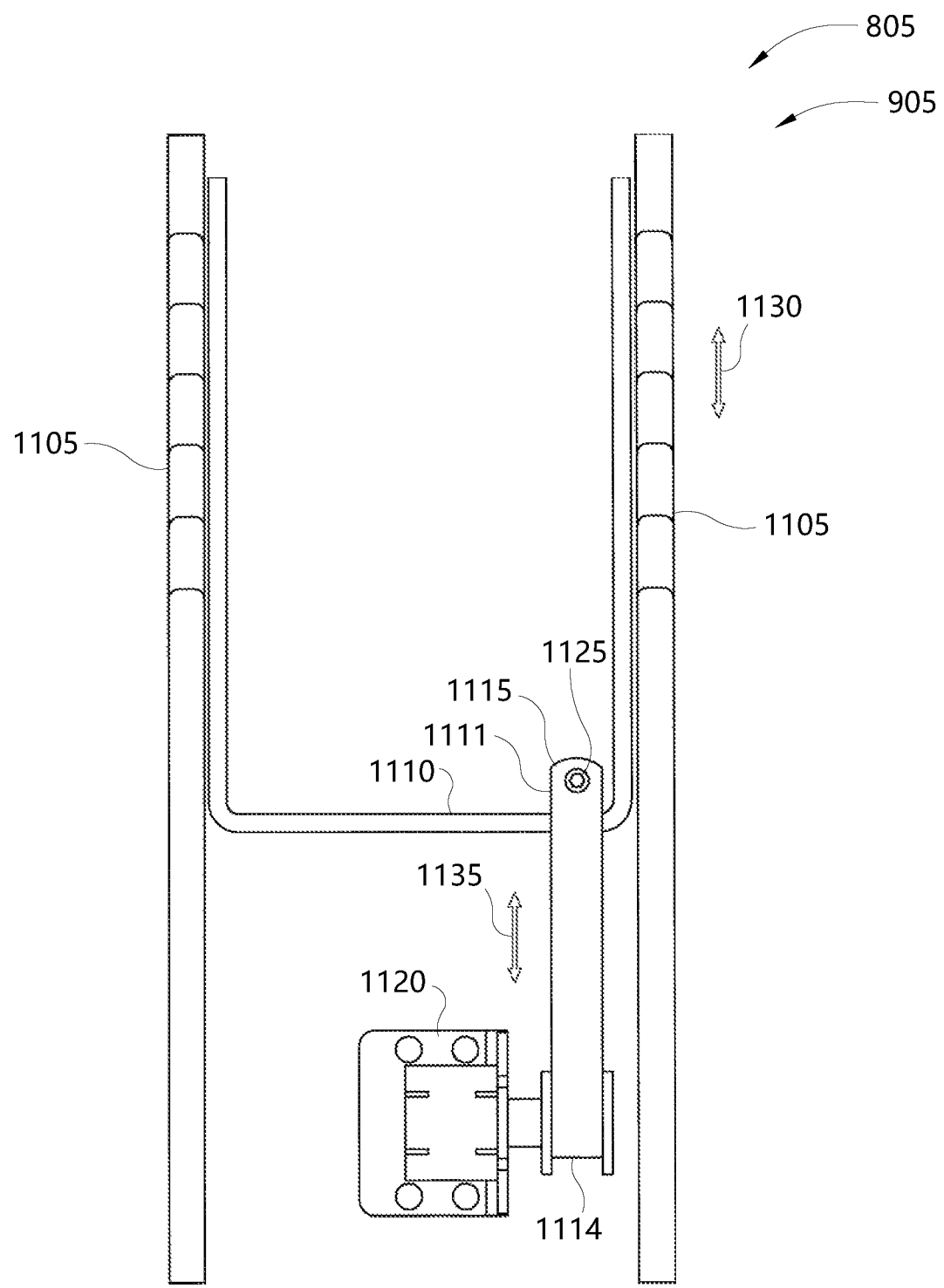
FIG. 11 is a front view of the headrest sensor assembly of FIG. 8 in the lowered position.
Figure 12:
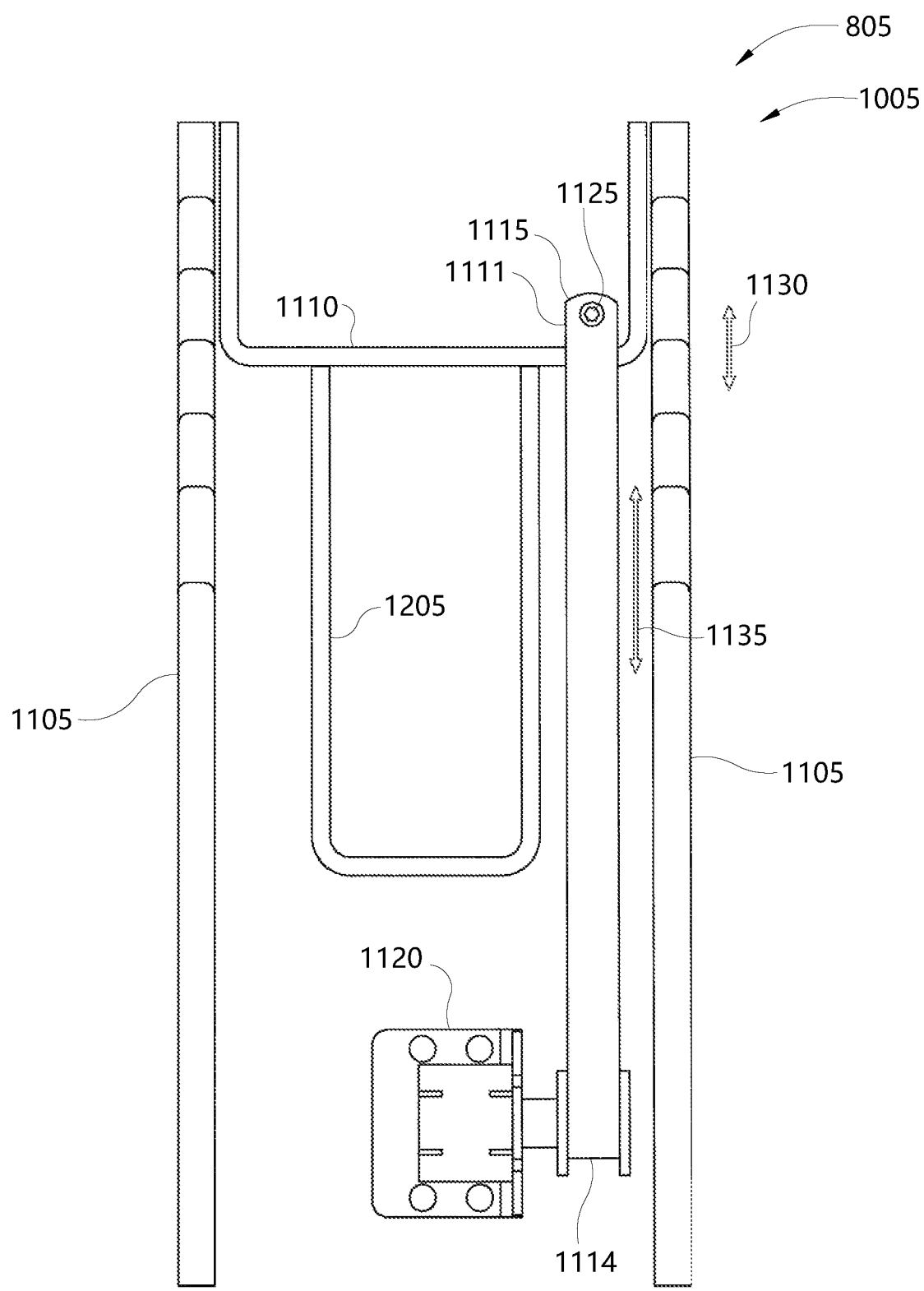
FIG. 12 is a front view of the headrest sensor assembly of FIG. 8 in the raised position.

FIGS. 11 and 12 show components of the headrest sensor assembly 805. The headrest sensor assembly 805 includes a pair of guides 1105. The guides 1105 are configured to telescope inwards and outwards to adjust the vertical position of the headrest 205. Using the guides 1105, the headrest 205 can be adjusted. For example, pulling on the headrest 205 raises the headrest 205 and pushing downwards on the headrest 205 lowers the headrest 205.

The headrest sensor assembly 805 further includes an adjustable rail 1110. The adjustable rail 1110 serves as a mounting position for a tape 1115. The tape 1115 is secured to the adjustable rail 1110 via a fastener 1125 at a first end 1111. The fastener 1125 may be a screw, bolt, nut, adhesive, rivet, weld, and/or other fastener. At a second end 1114, the tape 1115 is secured to headrest position sensor 125. In one embodiment, the headrest position sensor 125 is a rotary sensor 1120. The headrest position sensor 125 is configured to read the vertical position of the headrest 205. The headrest position sensor 125 can then transmit the position information to the processor 105. The processor 105 then determines whether the headrest 205 is in the correct position for the child.

As can be seen in FIG. 12, the headrest sensor assembly 805 further includes a brace 1205. The brace 1205 is configured to support the headrest 205 when in the raised position 1005. As indicated by arrow 1130, the headrest 205 is adjustable via the guides 1105. As the guides 1105 extend and/or retract, the tape 1115 extends and/or retracts as indicated by arrow 1135.

In one form, the rotary sensor 1120 is in the form of a digital rotary encoder such an optical incremental or absolute type rotary encoder. In another form, the rotary sensor 1120 includes a potentiostat. When the rotary sensor 1120 is in the form of a potentiostat, as the tape 1115 extends and/or retracts, the rotary sensor 1120 experiences a change in resistance, which leads to a change in voltage. This change in voltage is read by the processor 105. The change in voltage corresponds to a particular position of the headrest 205. Thus, the headrest position sensor 125 determines if the position of the headrest 205 matches the specified position (or position range) of the headrest 205 needed for proper child positioning.

Figure 13:
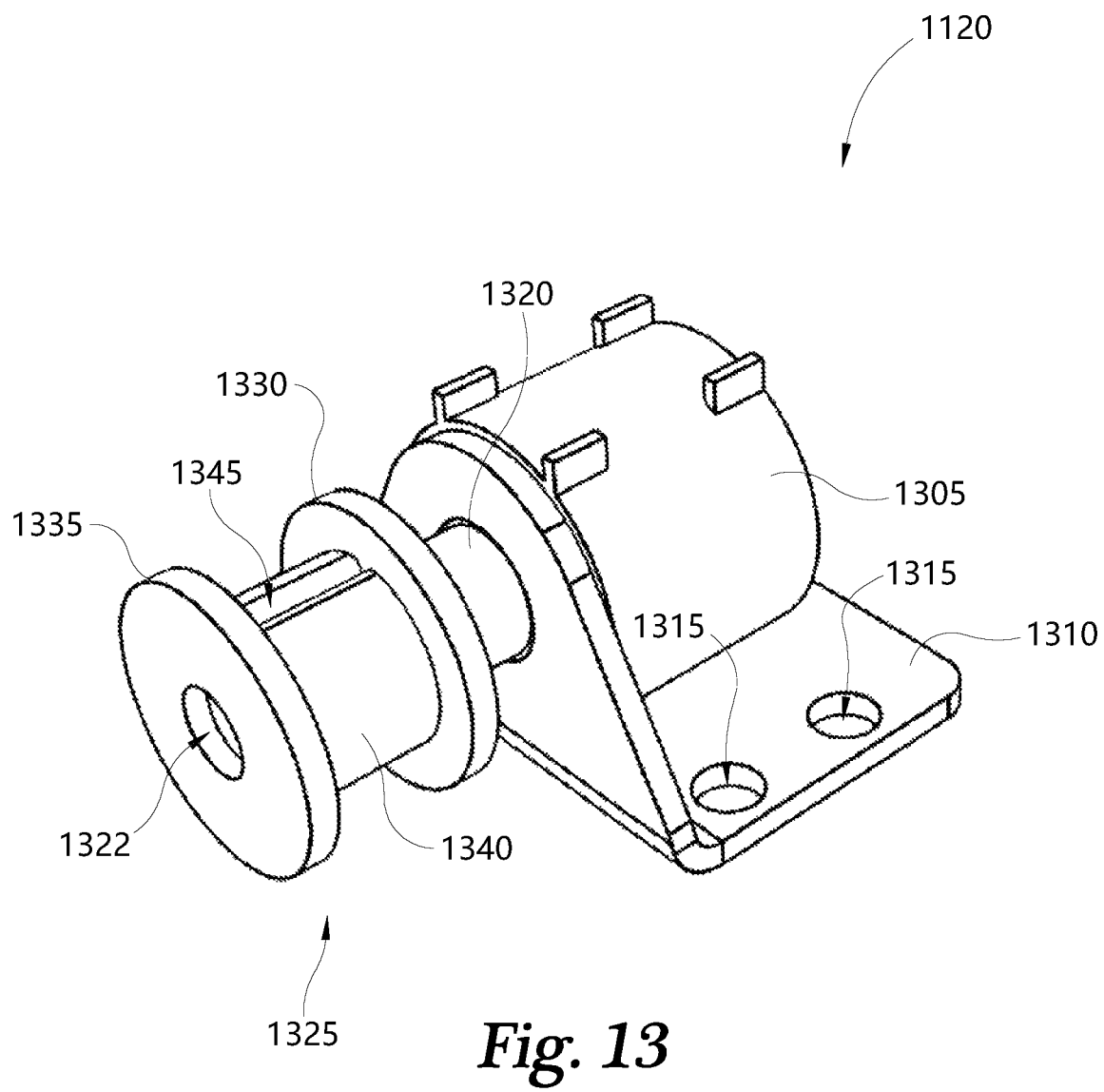
FIG. 13 is a perspective view of a rotary sensor used with the headrest sensor assembly of FIG. 8.

FIG. 13 shows an example of the rotary sensor 1120. The rotary sensor 1120 includes a body 1305 and a base 1310. The base 1310 includes one or more apertures 1315 configured to receive one or more fasteners. The fasteners may be a screw, bolt, nut, adhesive, rivet, weld, and/or other fastener. The rotary sensor 1120 is generally mounted to the interior portion 300 of the headrest 205 and/or the seat back 207 of the seat monitoring system 100. Put differently, the rotary sensor 1120 is mounted to the interior portion 300 of the seat monitoring system 100 in a stationary position, while the headrest 205 and tape 1115 are mounted in a movable position.

Extending from the body 1305 is an axle 1320. At one end of the axle 1320 includes a spool 1325. The spool 1325 is generally fixed to the axle 1320 such that as the spool 1325 rotates the axle 1320 rotates. As should be appreciated, the axle 1320 is rotatably mounted within the body 1305. In another example, the spool 1325 is rotatably mounted to the axle 1320. The spool 1325 generally includes an inner flange 1330 and an outer flange 1335. Located between the inner flange 1330 and the outer flange 1335 is a barrel 1340. The barrel 1340 further includes a slot 1345.

The tape 1115 is configured to extend within and mount inside of the slot 1345. In one example, the tape 1115 is held within the slot 1345 via a set screw. In another example, the tape 1115 is held within the slot 1345 via adhesive and/or another fastener. The spool 1325 generally mounts onto the axle 1320 via an arbor 1322. In one example, as the headrest 205 is pushed down, the tape 1115 shortens. As the tape 1115 shortens, the tape 1115 wraps around the barrel 1340. Thus, rotating the axle 1320 and adjusting the resistance of the rotary sensor 1120. In another example, as the headrest 205 is raised, the tape 1115 extends. As the tape 1115 extends, the tape 1115 unwraps from the barrel 1340. Thus, rotating the axle 1320 and adjusting the resistance of the rotary sensor 1120.

Figure 14:
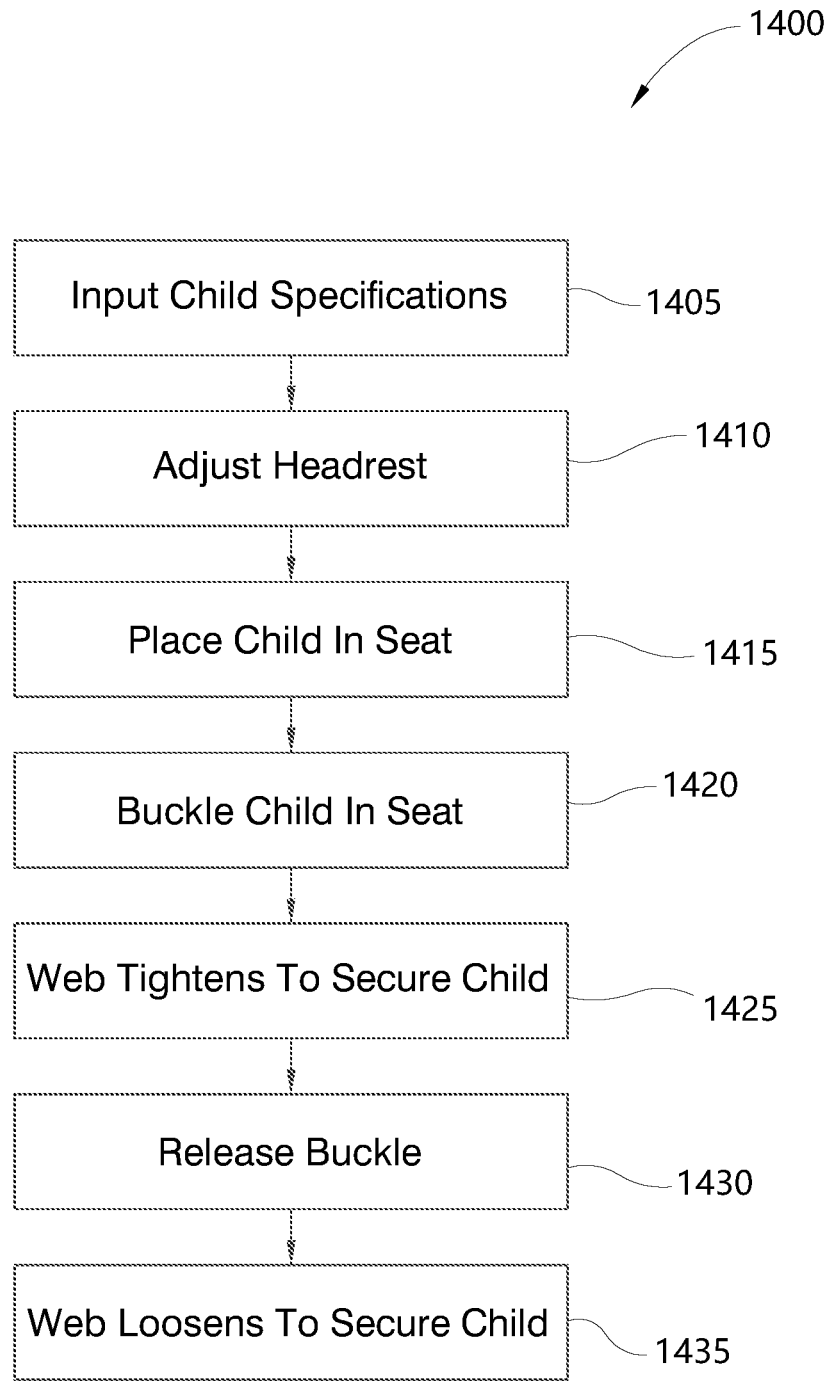
FIG. 14 is a flowchart of a child securing process.

FIG. 14 shows a flowchart 1400 of a process for properly securing a child in the child safety seat 200. At stage 1405, a user inputs child specifications for example, height, weight, age and/or other biometric information. In one example, the biometric information is inputted into the I/O device 120 and saved to the memory 110. In another example, the seat monitoring system 100 may not include an I/O device 120 and thus stage 1405 may be skipped. Based on the child specifications, a user may need to adjust the headrest 205 in stage 1410. For example, if the position of the headrest 205 is not correct the user will receive an alert via the I/O device 120. The alert may indicate how much to adjust the headrest 205.

After adjusting the headrest 205 to the proper position, the user places the child in the child safety seat 200 at stage 1415. After the child is placed in the child safety seat 200, the user secures the child by buckling the shoulder belts 225 and the buckle belt 235 via the latch plates 230 and the buckle 240 at stage 1420. The processor 105 determines proper fastening of the latch plates 230 and the buckle 240 via the buckle sensor 135. Once the buckle sensor 135 sends a buckle signal to the processor 105, the processor 105 commands the motor 145 to begin tensioning the shoulder belts 225 and the buckle belt 235 at stage 1425. The tension sensor 140 communicates tension information to the processor 105 during tensioning.

Once the proper tension level is reached, the processor 105 commands the motor 145 to stop tensioning. When a user is ready to remove the child from the child safety seat 200 the user unfastens the latch plates 230 and buckle 240 at stage 1430. After the latch plates 230 and buckle 240 are released, the buckle sensor 135 sends a signal to the processor 105. The processor 105 then commands the motor 145 to begin to loosen the shoulder belts 225 of the harness 222. Once a sufficient amount of slack is within the harness 222, the processor 105 commands the motor 145 to stop at stage 1435.

Figure 15:
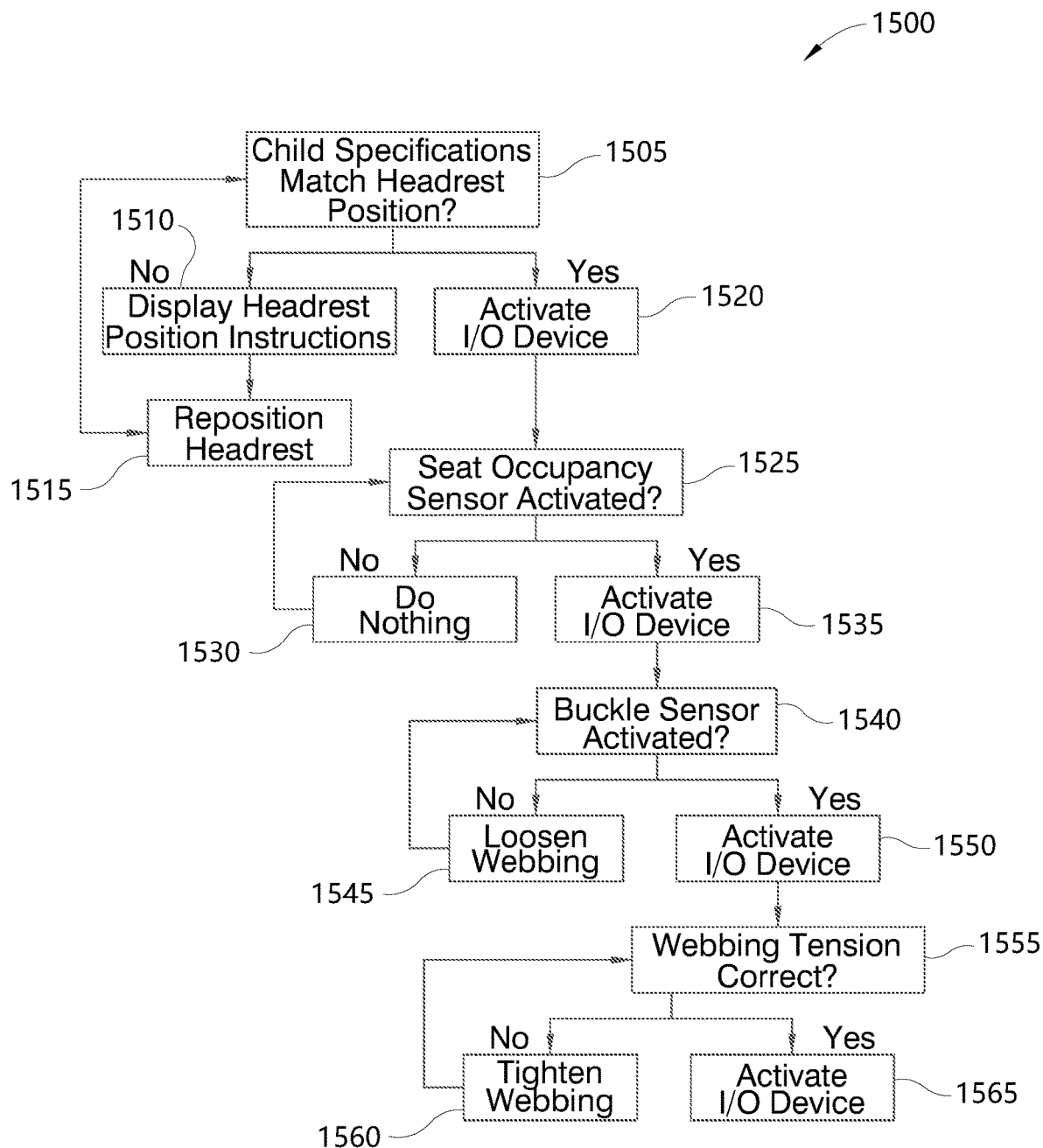
FIG. 15 is a flowchart of a processor logic process.
Figure 16:
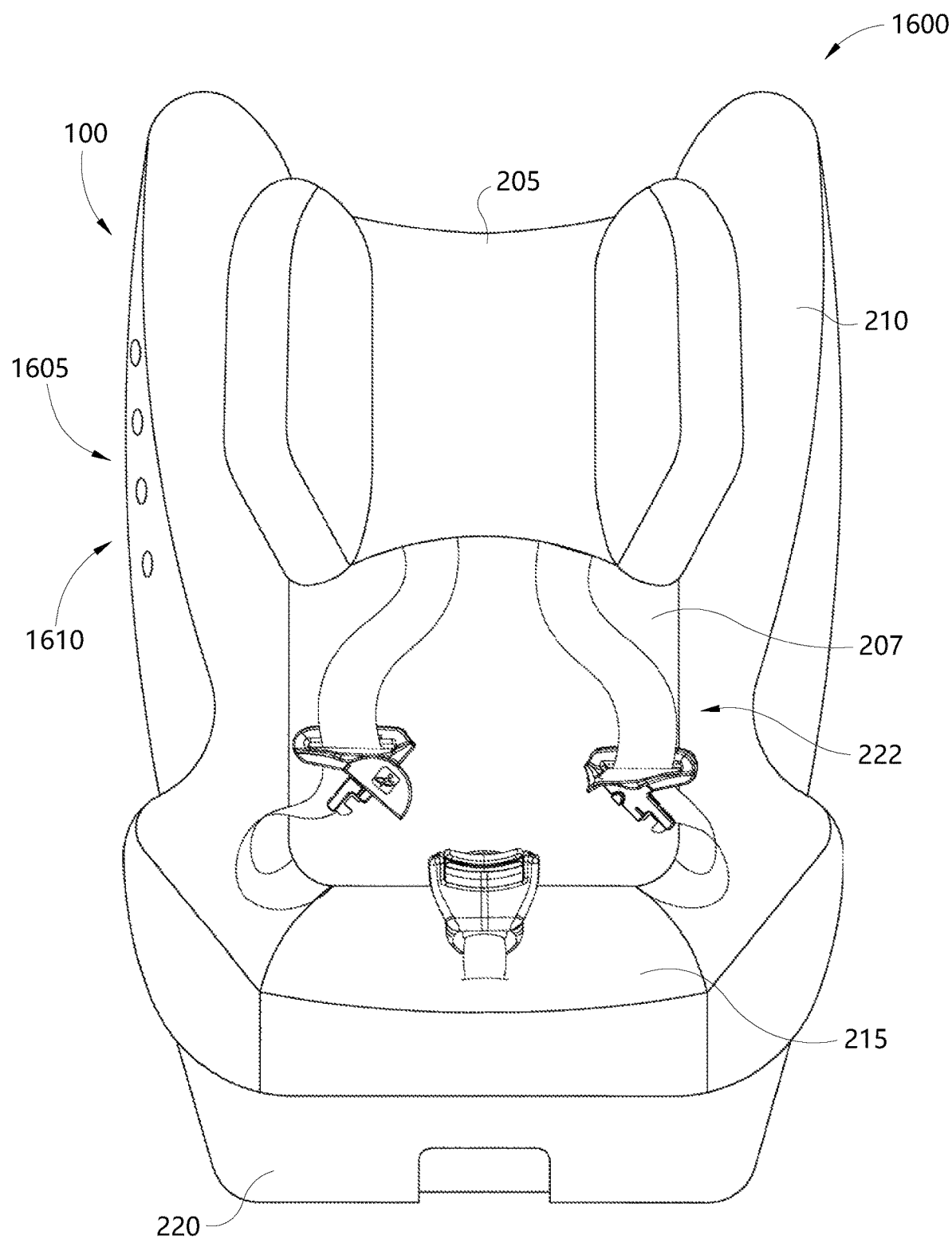
FIG. 16 is a front view of a child safety seat with an indicator system.

In FIG. 15, an example of a flowchart 1500 showing a logic process for the seat monitoring system 100. Generally, the logic processes shown in flowchart 1500 correspond with the child securing steps shown in flowchart 1400. At stage 1505, the processor 105 monitors the inputted child specifications to determine if they match the current position of the headrest 205. If the current position is not correct, according to the inputted child specifications, the I/O device 120 displays instructions to adjust the headrest 205 at stage 1510.

At stage 1515, the user repositions the headrest 205 into the proper position. Once the position of the headrest 205 matches the specified position (or within the range), the I/O device 120 provides a checkmark and/or other positive signal at stage 1520. At stage 1525 the occupant sensor 130 determines whether a child is placed in the seat. Generally, the occupant sensor 130 is a pressure sensor. If no child is detected in the child safety seat 200 the processor 105 does not act at stage 1530. If a child is detected in the seat monitoring system 100, the I/O device 120 displays a checkmark and/or other symbol indicating that a child is located within the seat monitoring system 100 at stage 1535.

At stage 1540 the buckle sensor 135 determines whether the latch plates 230 and/or the buckle 240 are properly fastened. The buckle sensor 135 is generally a reed sensor. If the latch plates 230 and/or buckle 240 are not fastened, the buckle sensor 135 notifies the processor 105. The processor 105 then commands the motor 145 to pay out slack in the harness 222 at stage 1545. If the latch plates 230 and the buckle 240 are properly fastened the I/O device 120 displays a checkmark and/or other signal at stage 1550. At stage 1555 the one or more tension sensor 140 determines the tension in the shoulder belts 225 and the buckle belt 235. For example, after the latch plates 230 and the buckle 240 are properly fastened, the motor 145 tightens the shoulder belts 225 and buckle belt 235 until reaching a specified tension or tension range read by the tension sensor 140.

If the tension in the shoulder belts 225 and buckle belt 235 is not high enough, the processor 105 commands the motor 145 to tighten the harness 222 at stage 1560. If the tension in the harness 222 matches the predetermined value, the I/O device 120 in stage 1565 provides a checkmark and/or other positive signal indicating that the child is properly secured within the seat monitoring system 100.

FIGS. 16, 17, 18, 19, 20, and 21 show one embodiment of a child safety seat 1600 that includes the seat monitoring system 100. The child safety seat 1600 includes an indicator system 1605. The indicator system 1605 includes at least one light emitting diode (LED) 1610. The indicator system 1605 is a visual indicator of completion of each stage of the child insertion and securing process. In one example, the indicator system 1605 includes light emitting diodes 1610. In other examples, the indicator system 1605 may include other types of visual and/or audial signals.

Figure 17:
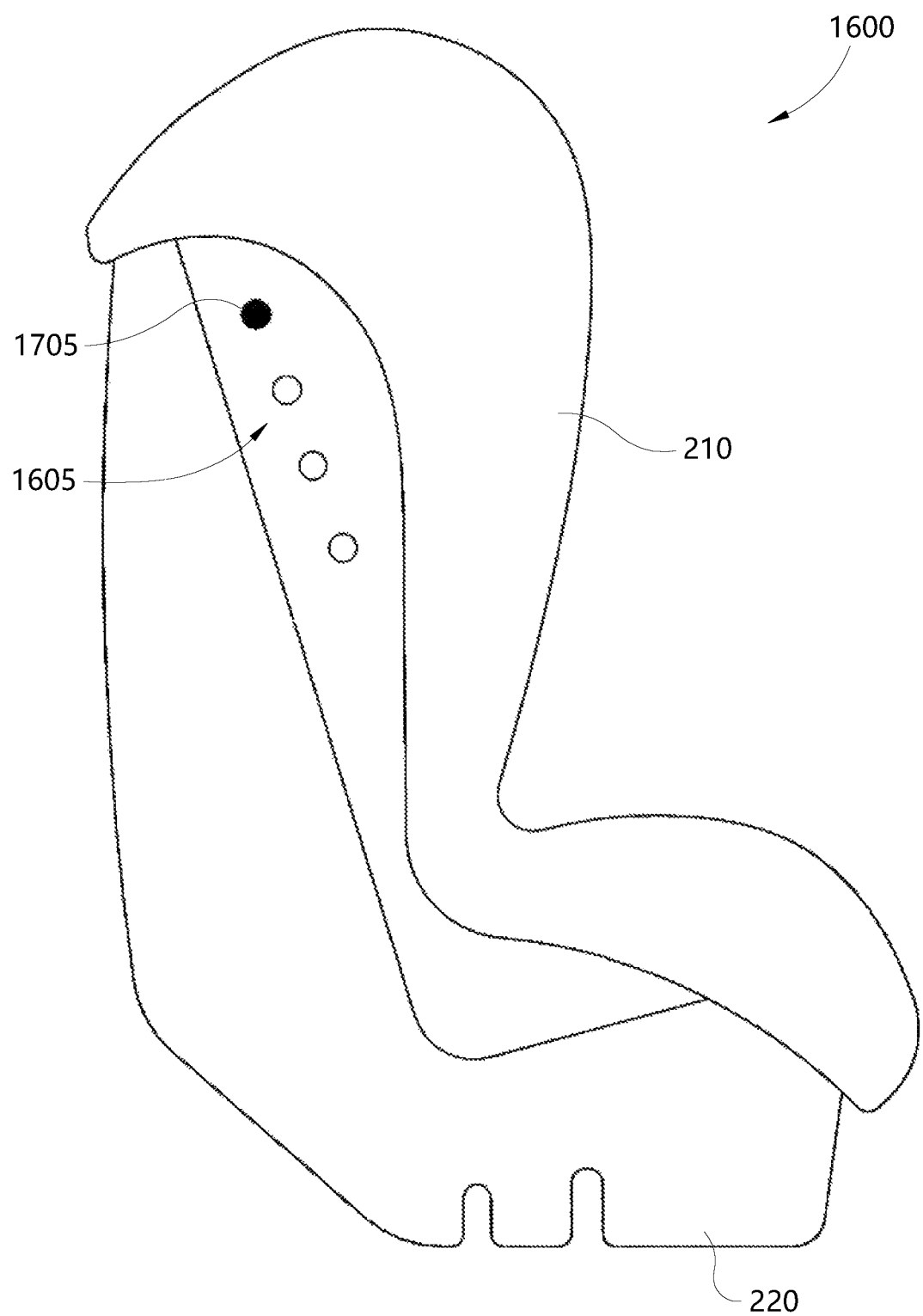
FIG. 17 is a front view of the child safety seat of FIG. 16.
Figure 18:
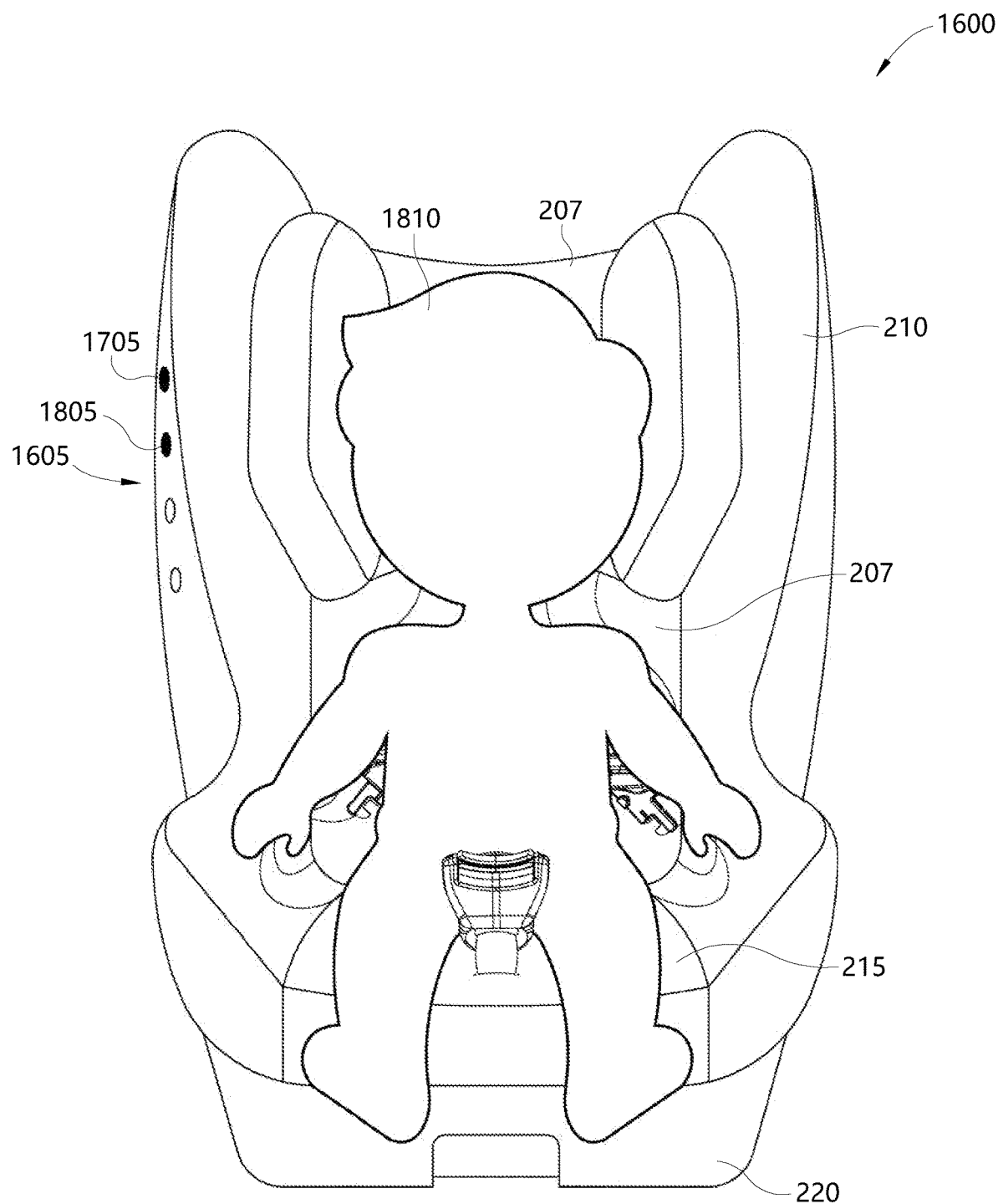
FIG. 18 is a front view of the child safety seat of FIG. 16.
Figure 19:
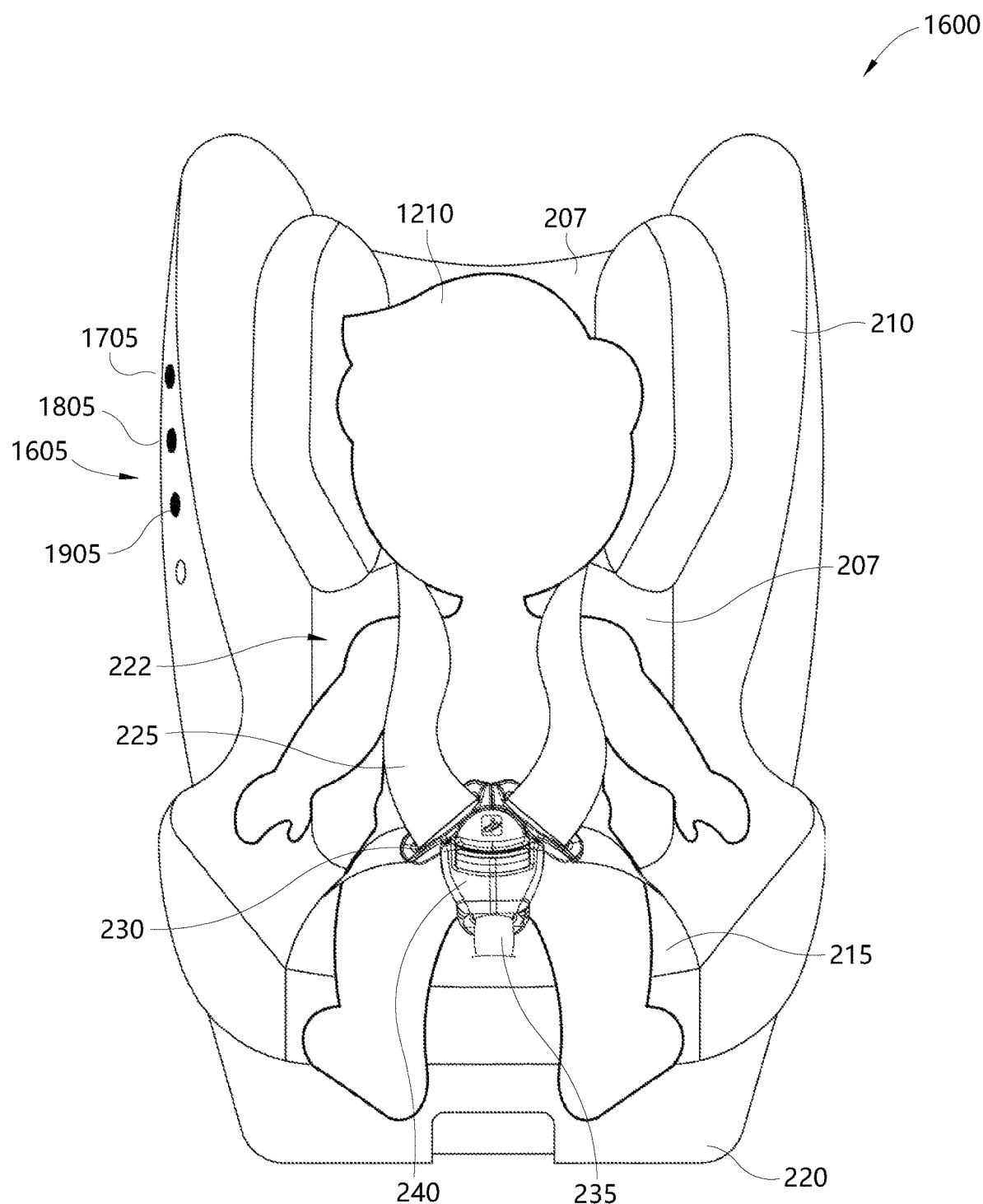
FIG. 19 is a front view of the child safety seat of FIG. 16.

In FIG. 17, the indicator system 1605 is shown with an illuminated first LED 1705. The illuminated first LED 1705 indicates that the position of the headrest 205 is correct and no movement of the headrest 205 is needed. In another embodiment, illumination of the first LED 1705 indicates that the position of the headrest 205 is not correct and that the headrest 205 needs to be adjusted by a user. In FIG. 18, the indicator system 1605 is shown with both the first LED 1705 and a second LED 1805 illuminated. The illuminated second LED 1805 indicates that a child 1810 is seated within the child safety seat 1600. For example, the child 1810 may be detected via the occupant sensor 130. In FIG. 19, the first LED 1705, the second LED 1805, and a third LED 1905 of the indicator system 1605 are all illuminated. The illuminated third LED 1905 indicates that the latch plates 230 and buckle 240 are properly fastened. Put differently, the third LED 1905 indicates to a user that the child 1810 is buckled. Proper buckling is determined using the buckle sensor 135, which is generally in the form of a reed switch.

Figure 20:
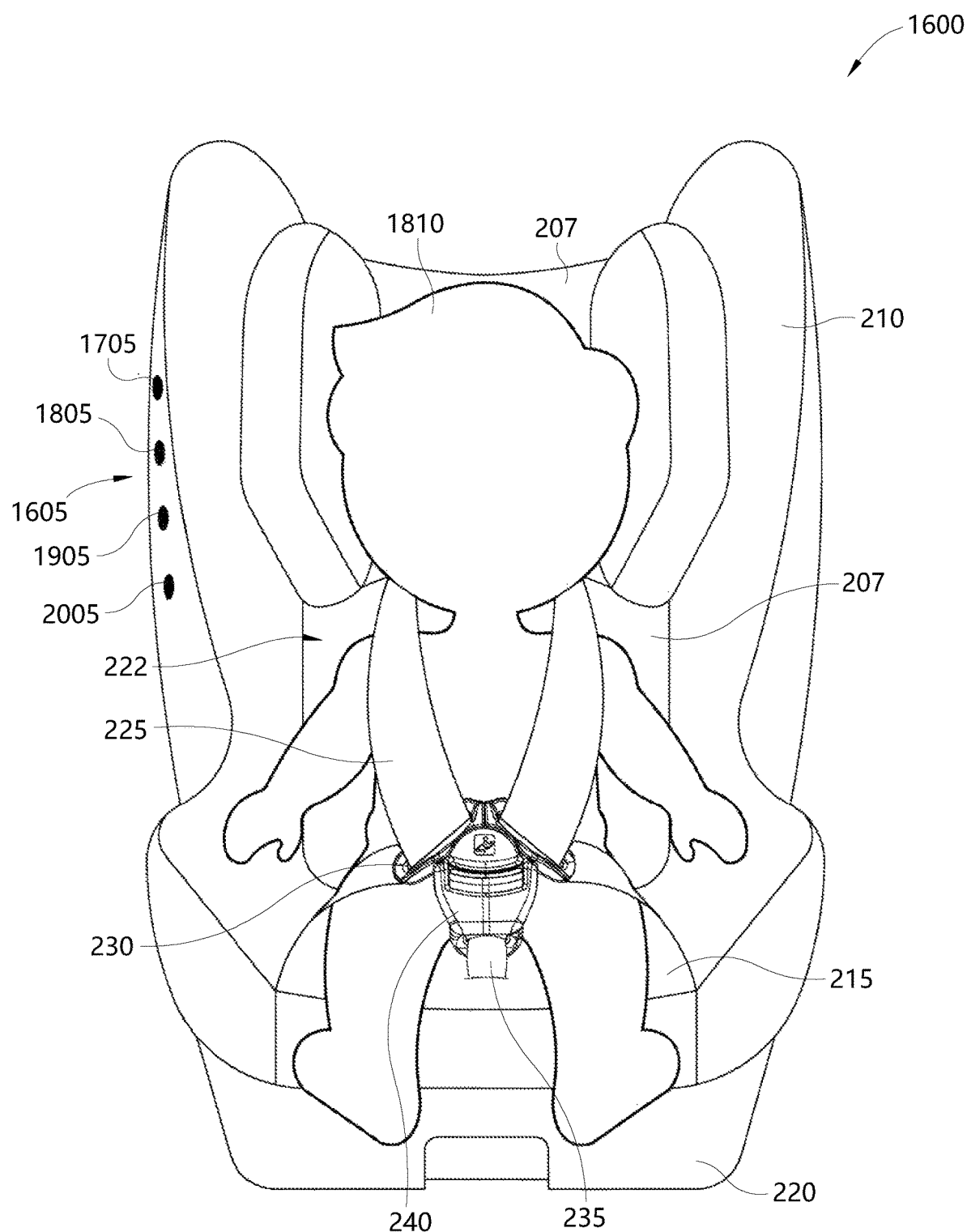
FIG. 20 is a front view of the child safety seat of FIG. 16.

In FIG. 20, the first LED 1705, the second LED 1805, the third LED 1905, and a fourth LED 2005 of the indicator system 1605 are all illuminated. The illuminated fourth LED 2005 indicates that the shoulder belts 225 and buckle belt 235 are properly tensioned. As has been mentioned previously, the harness 222 is tightened automatically by one or more motors 145. The tension of the shoulder belts 225 and the buckle belt 235 is controlled via one or more tension sensors 140 in communication with the processor 105. Additionally, the illumination of all of the indicator system 1605 indicates to a user that the child 1810 is properly secured within the child safety seat 1600.

Figure 21:
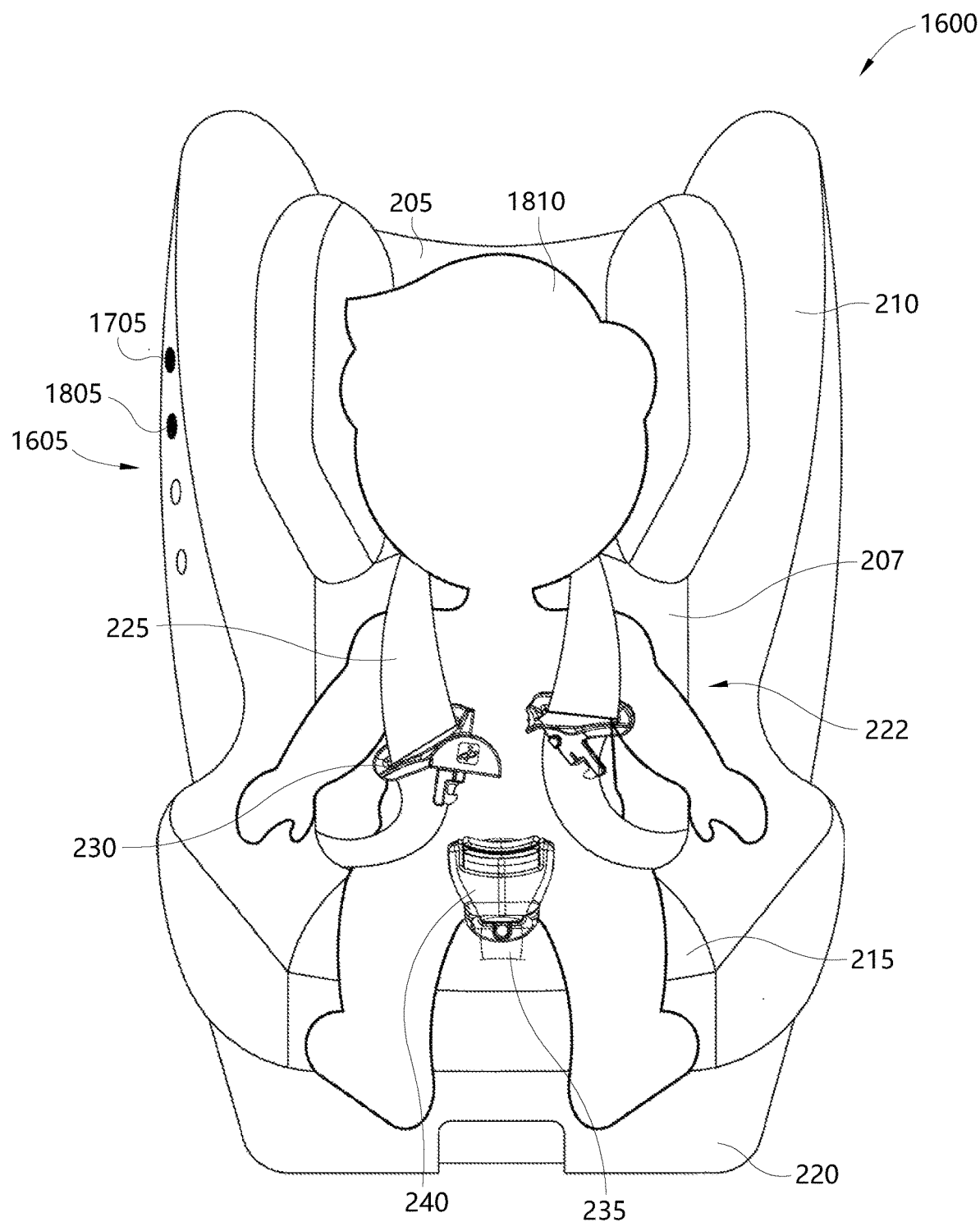
FIG. 21 is a front view of the child safety seat of FIG. 16.

FIG. 21 shows an example of a child unbuckling event. When the latch plates 230 and buckle 240 are unbuckled the indicator system 1605 returns to only illuminating the first LED 1705 and the second LED 1805. At the same time, the processor 105 commands the motors 145 to loosen the harness 222 to enable a user to remove the child 1810 from the child safety seat 1600. As should be appreciated, the light emitting diodes 1610 of the indicator system 1605 do not need to illuminate in order. For example, the second LED 1805 and the third LED 1905 may be illuminated without the first LED 1705 being illuminated.

Figure 22:
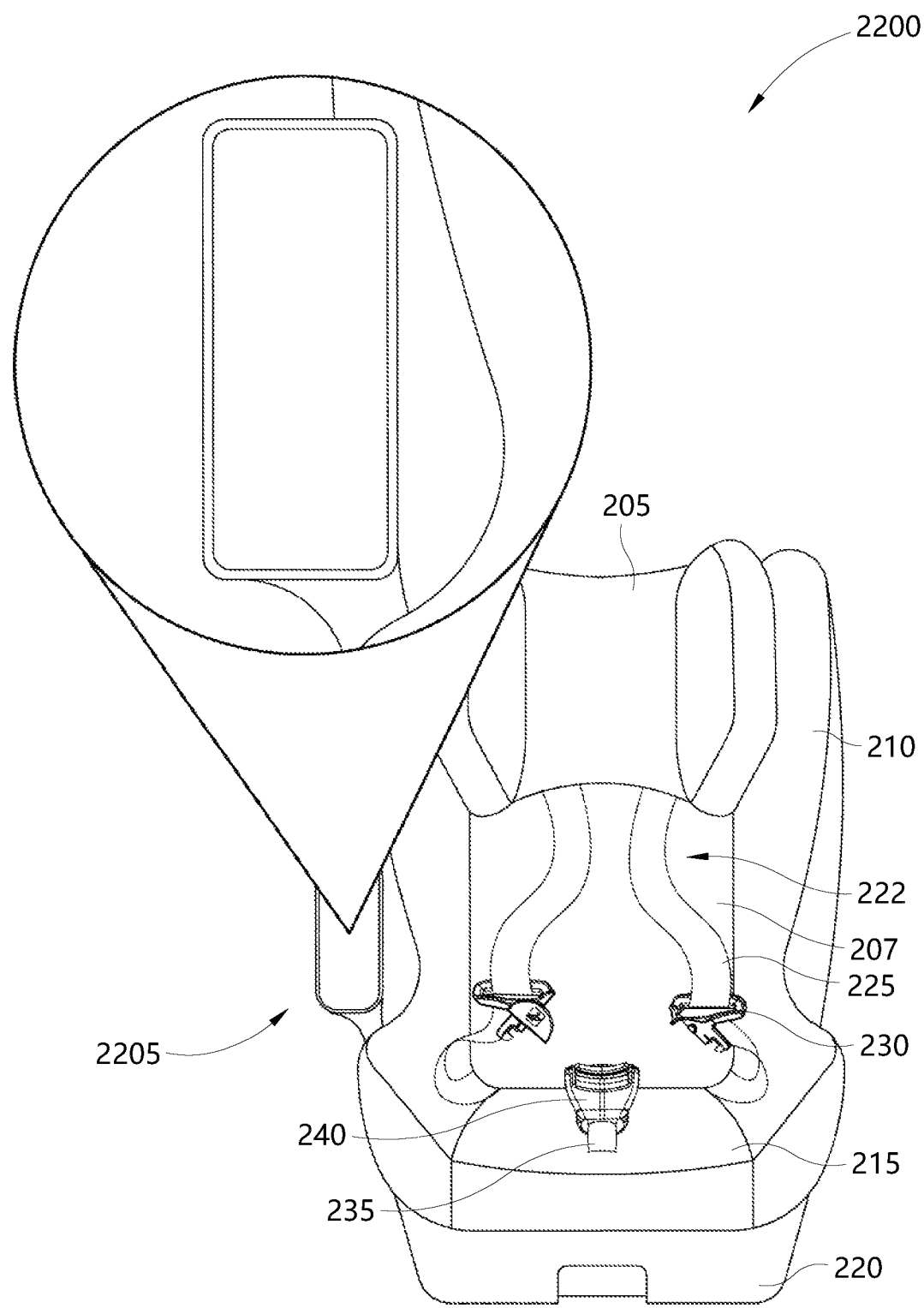
FIG. 22 is a front view of a child safety seat with a display.
Figure 23:
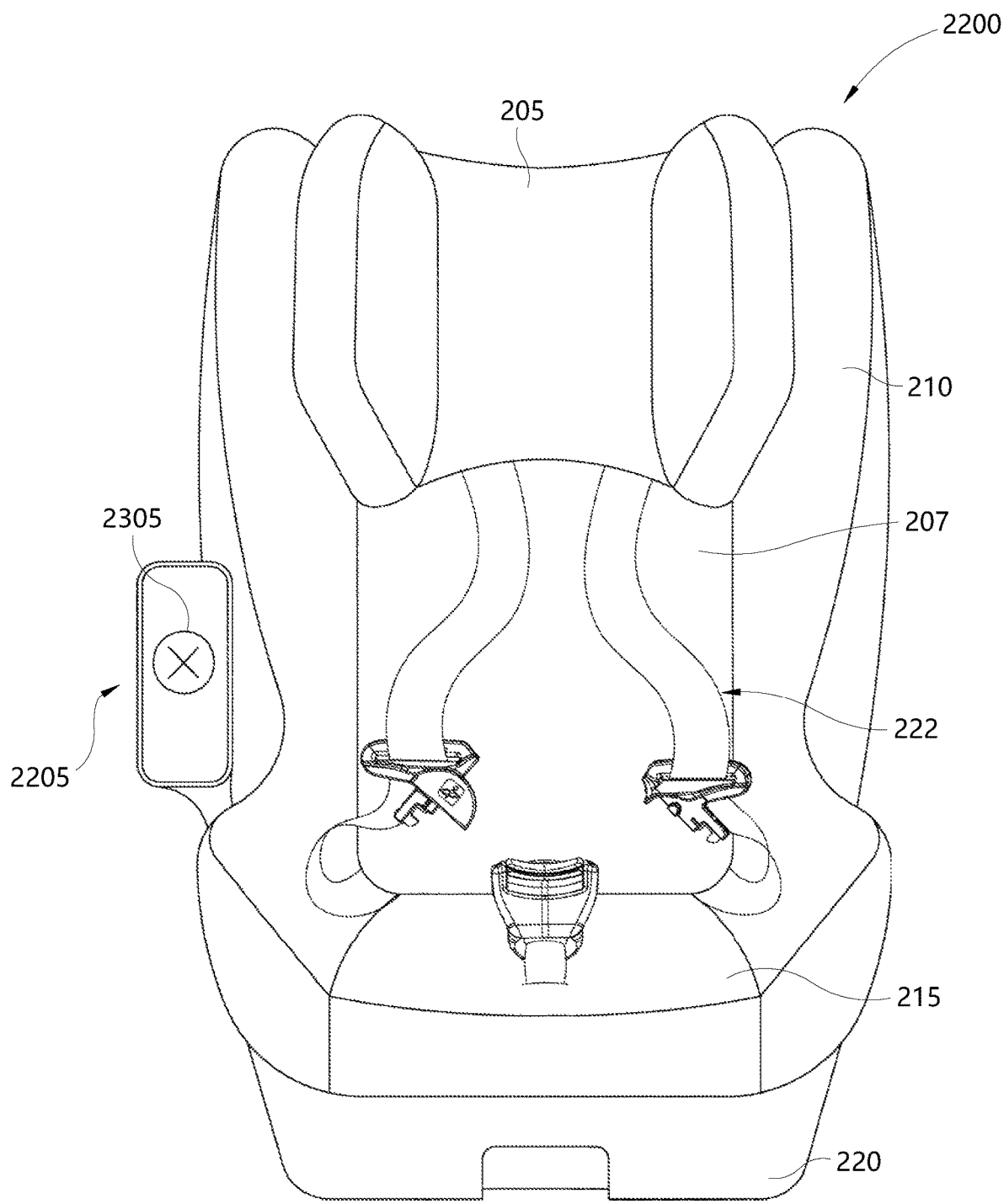
FIG. 23 is a front view of the child safety seat of FIG. 22.

FIGS. 22, 23, 24, 25, 26, 27, and 28 show another example of a child safety seat 2200 that includes the seat monitoring system 100. The child safety seat 2200 includes a display 2205 (i.e., I/O device 120). In FIG. 22, the child safety seat 2200 is in a dormant state. In the dormant state, the harness 222 is loose and the latch plates 230 and buckle 240 are unbuckled. Additionally, in the dormant state, a user can input child specifications into the display 2205. For example, a user may input child biometric information. In FIG. 23, the display 2205 is shown with a first status indicator 2305. The first status indicator 2305 indicates that the child safety seat 2200 is in the dormant state. For example, the first status indicator 2305 shows a red X and/or other visual signal.

Figure 24:
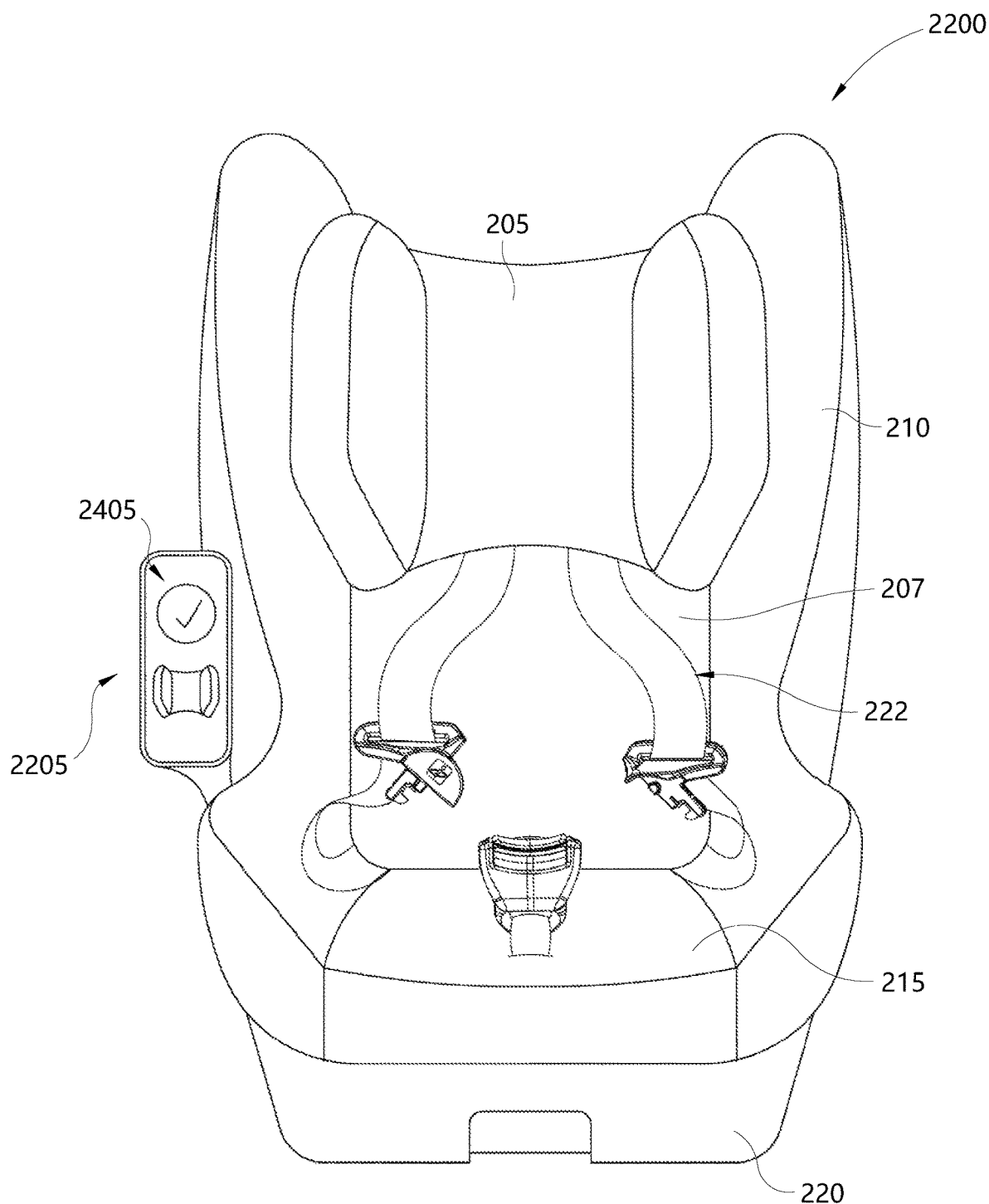
FIG. 24 is a front view of the child safety seat of FIG. 22.

In FIG. 24, the display 2205 is shown with a second status indicator 2405. The second status indicator 2405 indicates whether the position of the headrest 205 is correct and/or incorrect according to the inputted child specifications. In one embodiment, the display 2205 may display the needed adjustment for the headrest 205. However, in FIG. 24, the headrest 205 has been properly adjusted by a user. For example, the headrest position sensor 125 determined that the headrest 205 is in the proper position. The display 2205 displays a second status indicator 2405 indicating a checkmark or other positive indicator and a photo of the headrest 205 showing that the headrest 205 is properly positioned. If the headrest 205 is not properly positioned, the display 2205 displays a red X and/or other negative signal.

Figure 25:
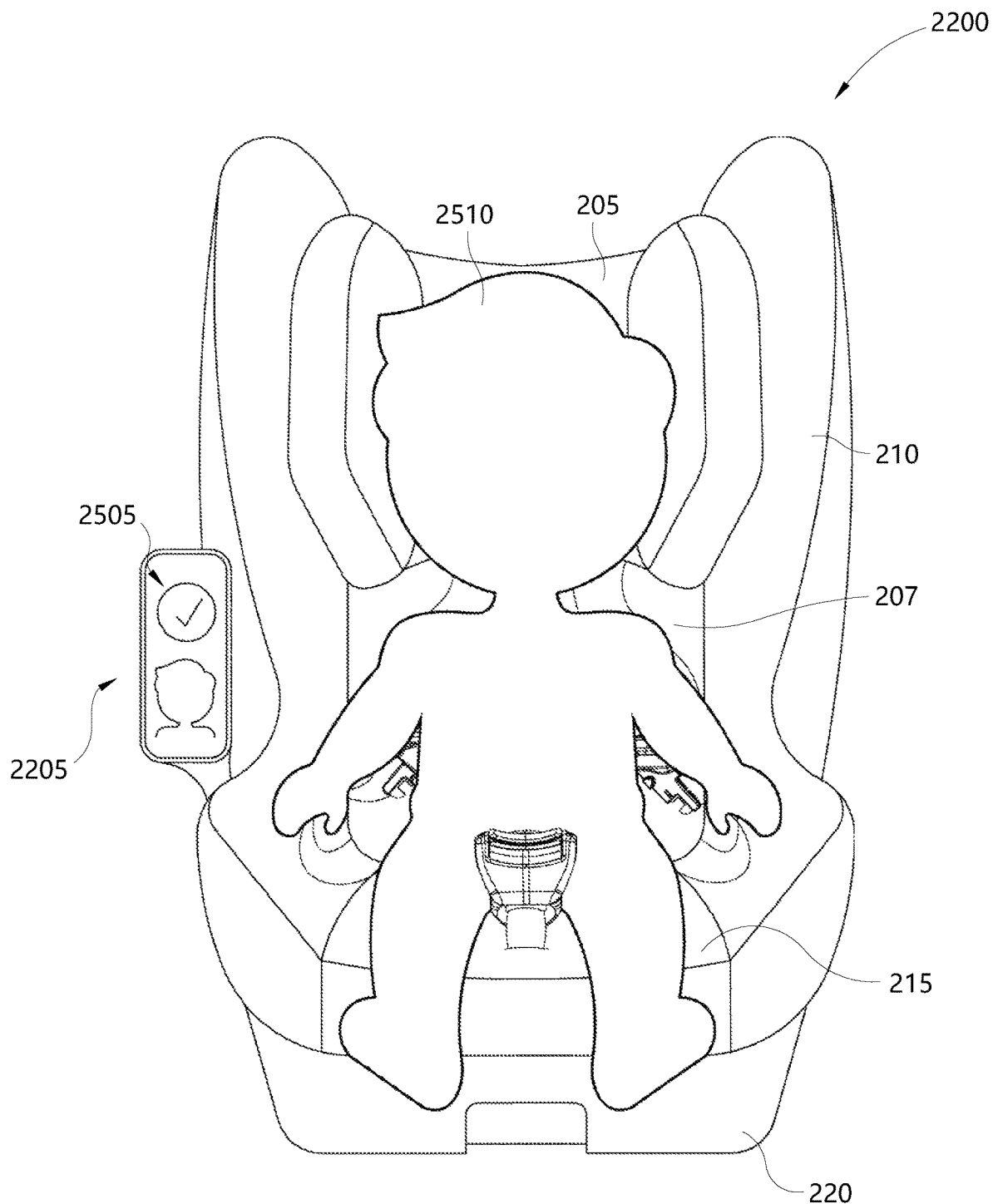
FIG. 25 is a front view of the child safety seat of FIG. 22.
Figure 26:
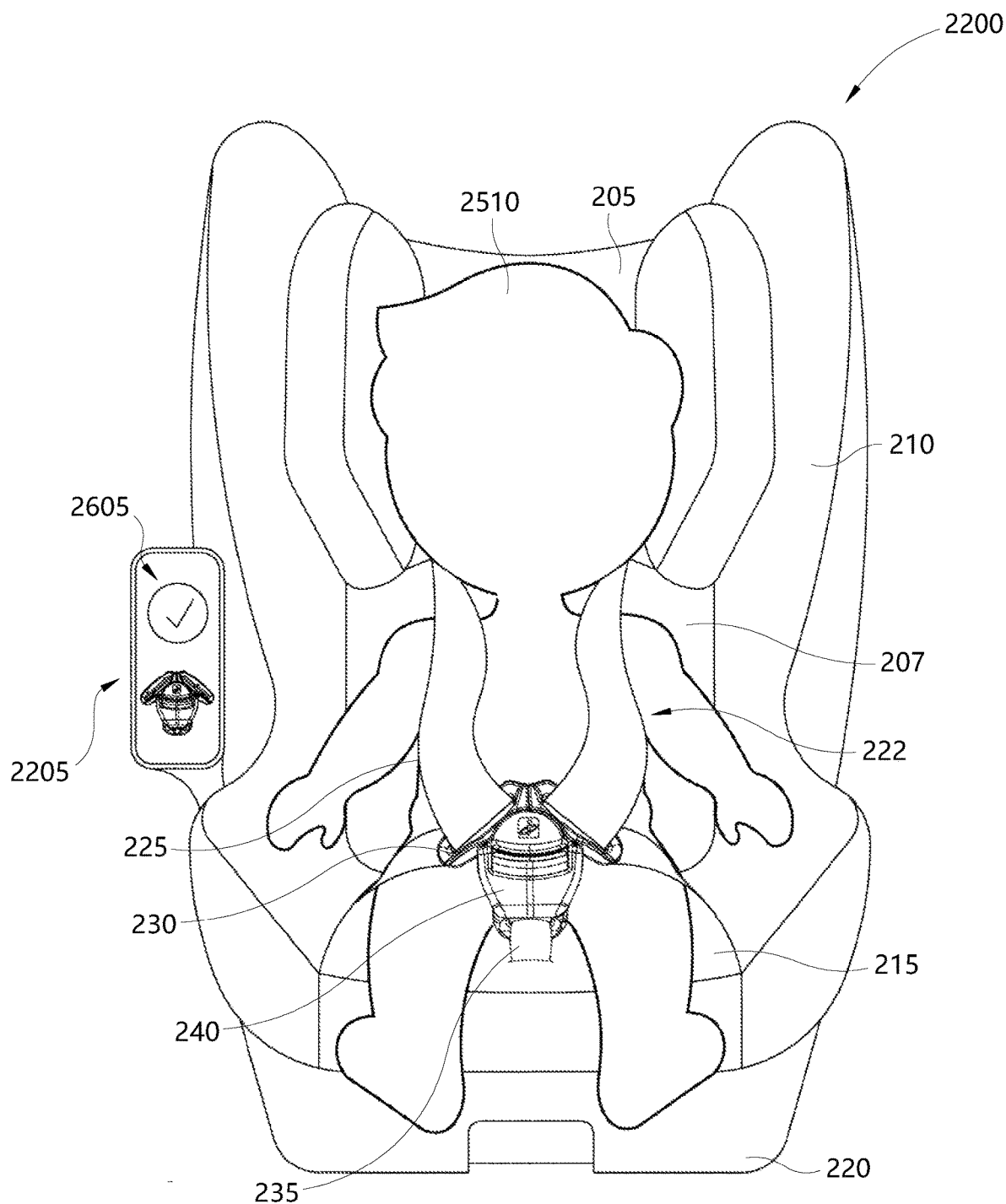
FIG. 26 is a front view of the child safety seat of FIG. 22.

At FIG. 25, the display 2205 displays a third status indicator 2505. The third status indicator 2505 displays a photo of a child and a positive mark and/or checkmark. The third status indicator 2505 indicates that the occupant sensor 130 determines a child 2510 is positioned within the child safety seat 2200. If a child 2510 is not in the child safety seat 2200, the third status indicator 2505 displays a red X and/or other negative signal. At FIG. 26, the display 2205 displays a fourth status indicator 2605. The fourth status indicator 2605 indicates that the latch plates 230 and the buckle 240 are properly buckled. The fourth status indicator 2605 generally includes an image of the latch plates 230 and/or buckle 240 and a checkmark and/or other positive signal indicating that the latch plates 230 and buckle 240 are properly fastened and connected. If the latch plates 230 and the buckle 240 are not properly fastened, the display 2205 displays a red X and/or other negative signal.

Figure 27:
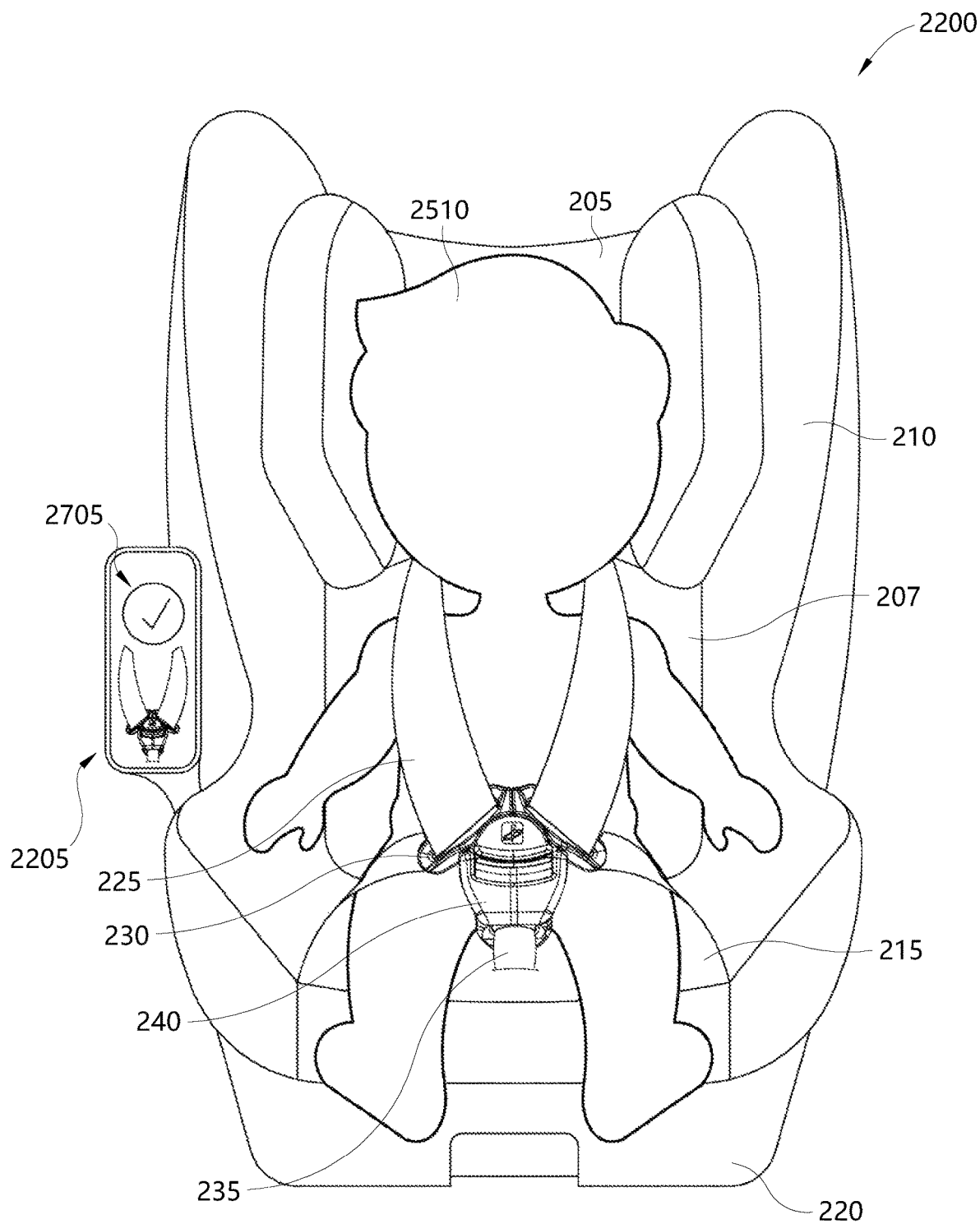
FIG. 27 is a front view of the child safety seat of FIG. 22.

At FIG. 27, the display 2205 displays fifth status indicator 2705. The fifth status indicator 2705 shows an image of the harness 222 as well as a checkmark and/or other positive signal indicating that the harness 222 is properly tensioned. The fifth status indicator 2705 may also indicate that the child 2510 is properly secured within the child safety seat 2200. If the shoulder belts 225 are not properly tensioned, the display 2205 displays a red X and/or other negative signal. Additionally, the processor 105 commands the motors 145 to tighten the shoulder belts 225 and the buckle belt 235.

Figure 28:
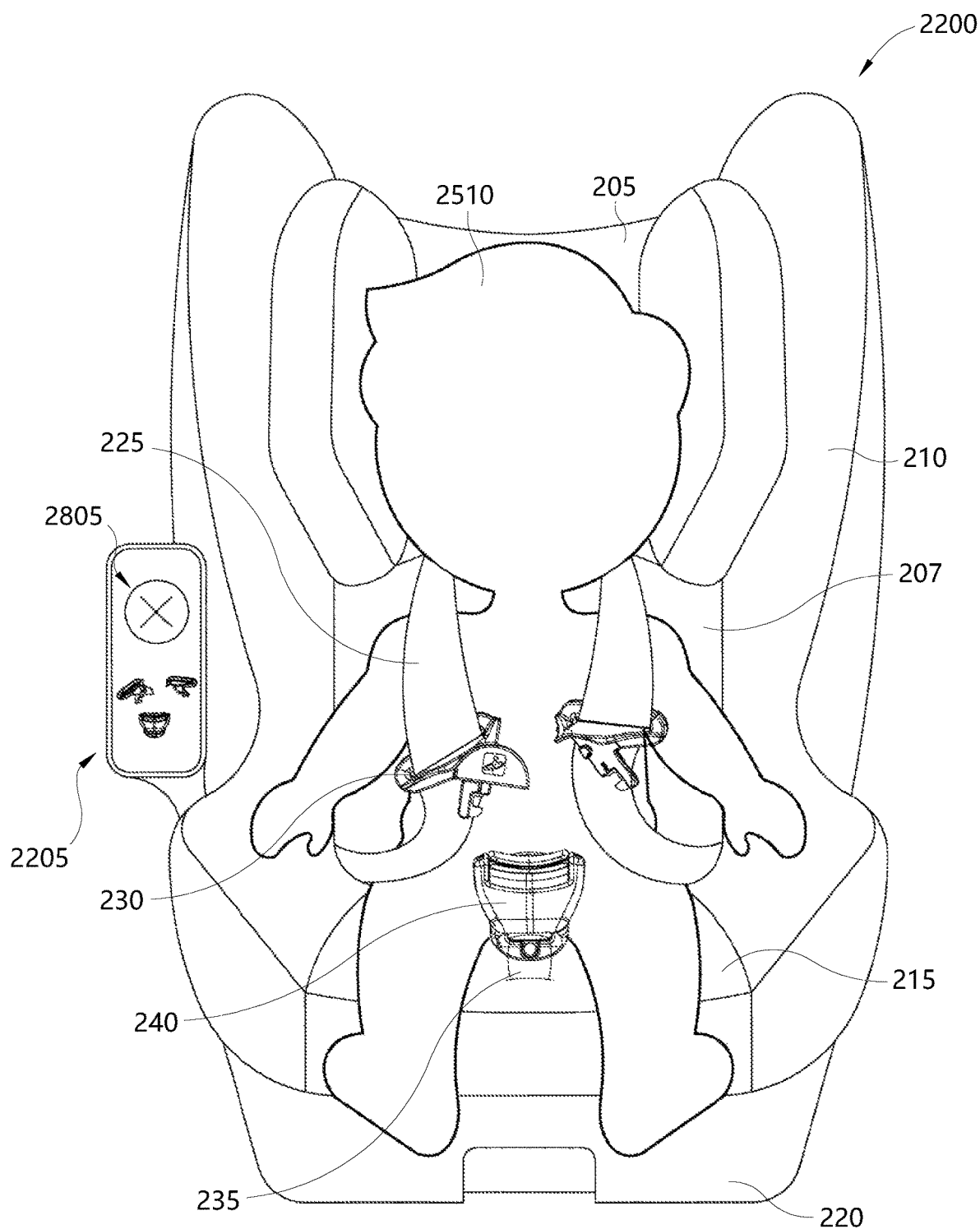
FIG. 28 is a front view of the child safety seat of FIG. 22.

At FIG. 28, the display 2205 displays a sixth status indicator 2805. The sixth status indicator 2805 shows an image of the latch plates 230 and buckle 240 and a negative remark and/or "X" showing that the latch plates 230 and buckle 240 are unbuckled. When the latch plates 230 and buckle 240 are unbuckled, the harness 222 is loosened to enable a user to remove the child 2510 from the child safety seat 2200.

Figure 29:
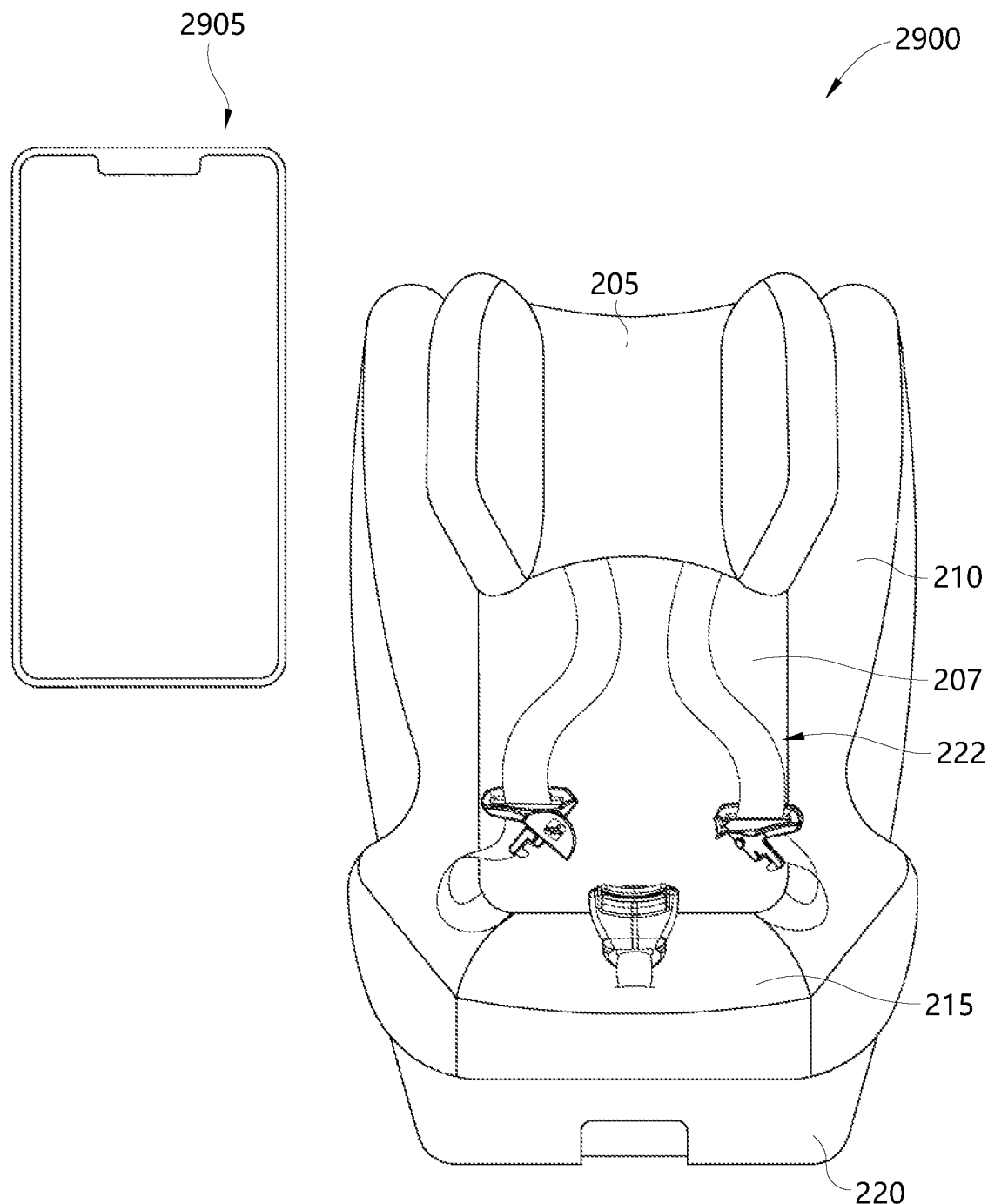
FIG. 29 is a front view of a child safety seat with a mobile device.
Figure 30:
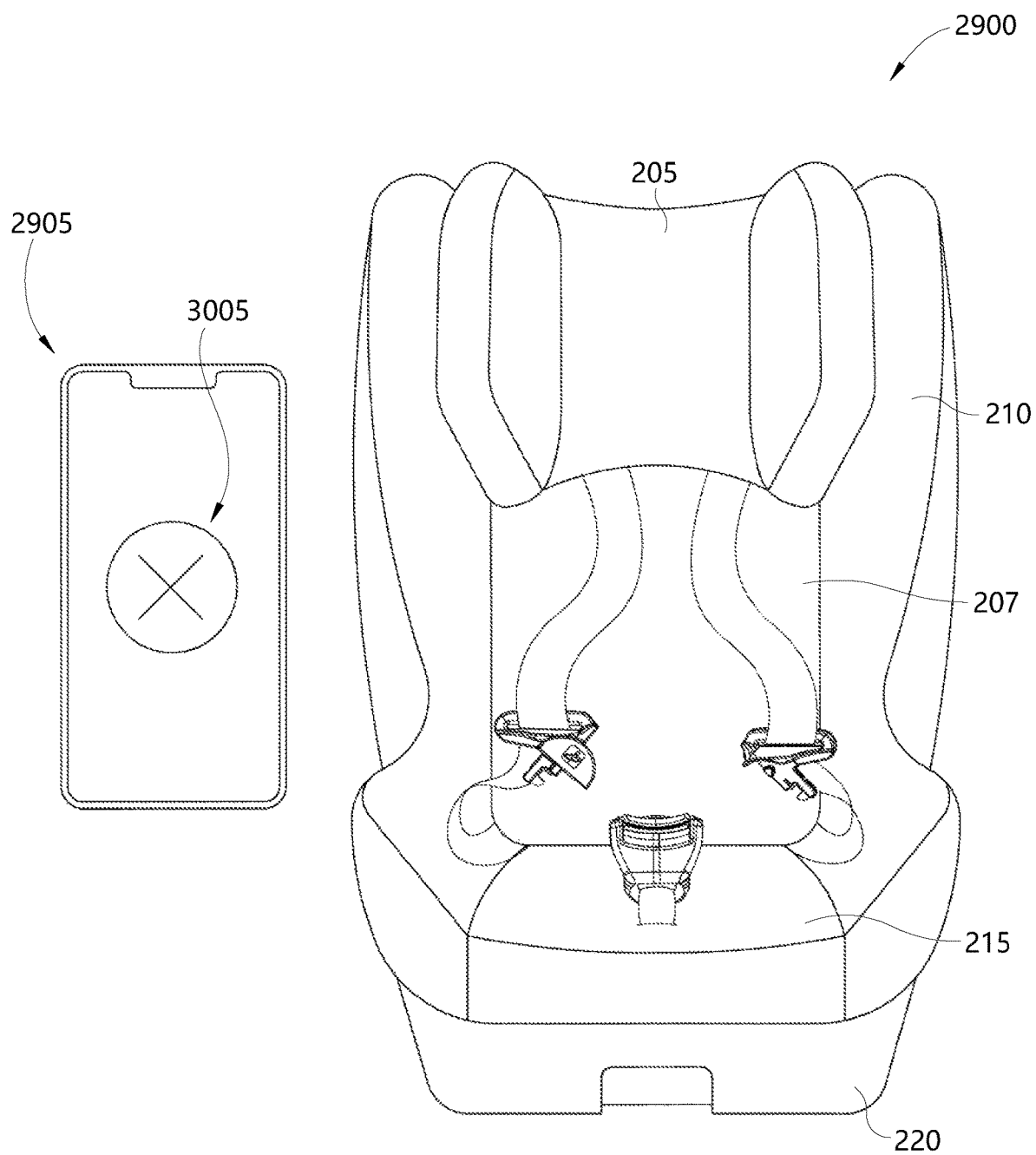
FIG. 30 is a front view of the child safety seat of FIG. 29.

FIGS. 29, 20, 31, 32, 33, 34, and 35 show a further example of a child safety seat 2900 that includes the seat monitoring system 100. The child safety seat 2900 includes a mobile device 2905. The mobile device 2905 may be a cellular device, such as a cell phone and/or tablet. Generally, the mobile device 2905 includes a mobile application (app) to access software for the child safety seat 2900. In FIG. 29, the child safety seat 2900 is in a dormant state. In the dormant state, a user may input child or infant specifications into the mobile device 2905 via the app. In FIG. 30, the mobile device 2905 is depicts a first status indicator 3005. The first status indicator 3005 indicates that the child safety seat 2900 is in the dormant state. For example, the mobile device 2905 shows a red X and/or other visual signal that the child safety seat 2900 is not in use.

Figure 31:
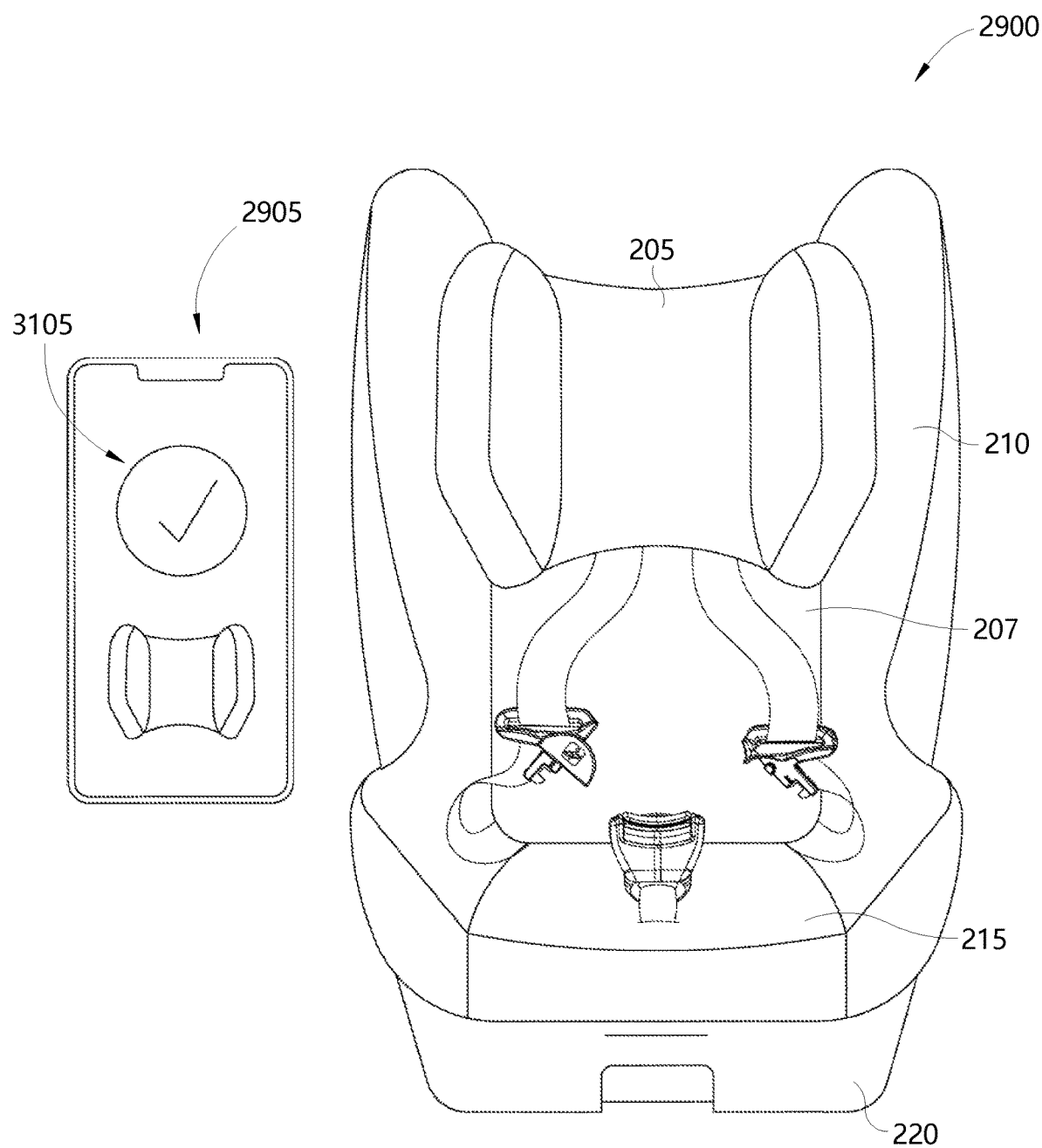
FIG. 31 is a front view of the child safety seat of FIG. 29.

In FIG. 31, the mobile device 2905 is shown to depict a second status indicator 3105. The second status indicator 3105 indicates the position of the headrest 205 according to the child specifications. Put differently, the second status indicator 3105 indicates whether the headrest 205 needs to be adjusted to match the child specifications. In one example, the mobile device 2905 may display the adjustment needed for the headrest 205. In another example, the mobile device 2905 may display a photo of the headrest 205 and/or a positive indicator and/or checkmark indicating that the position of the headrest 205 is correct. In yet another example, the mobile device 2905 displays a red X and/or other negative indicator indicating that the position of the headrest 205 is incorrect.

Figure 32:
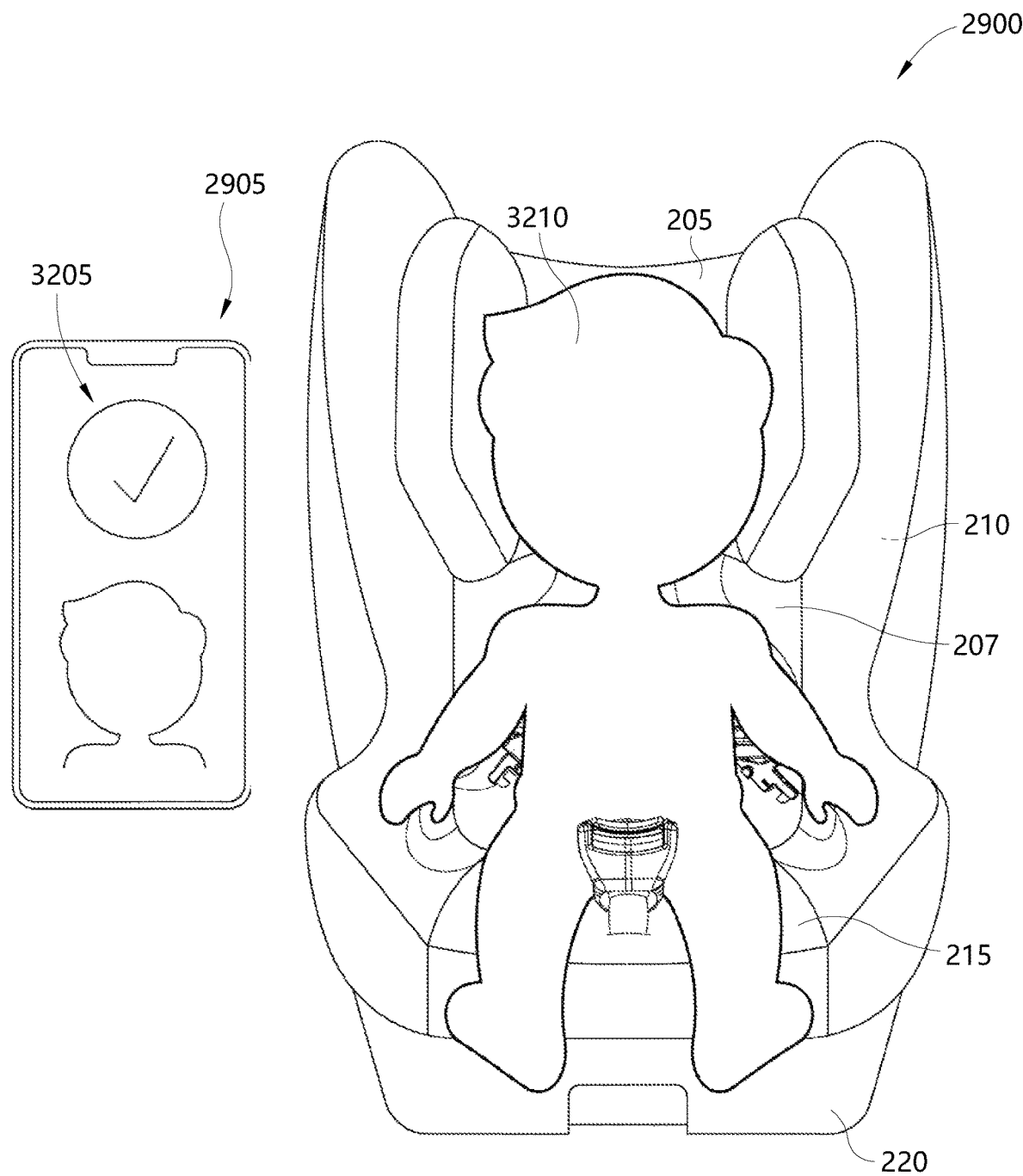
FIG. 32 is a front view of the child safety seat of FIG. 29.
Figure 33:
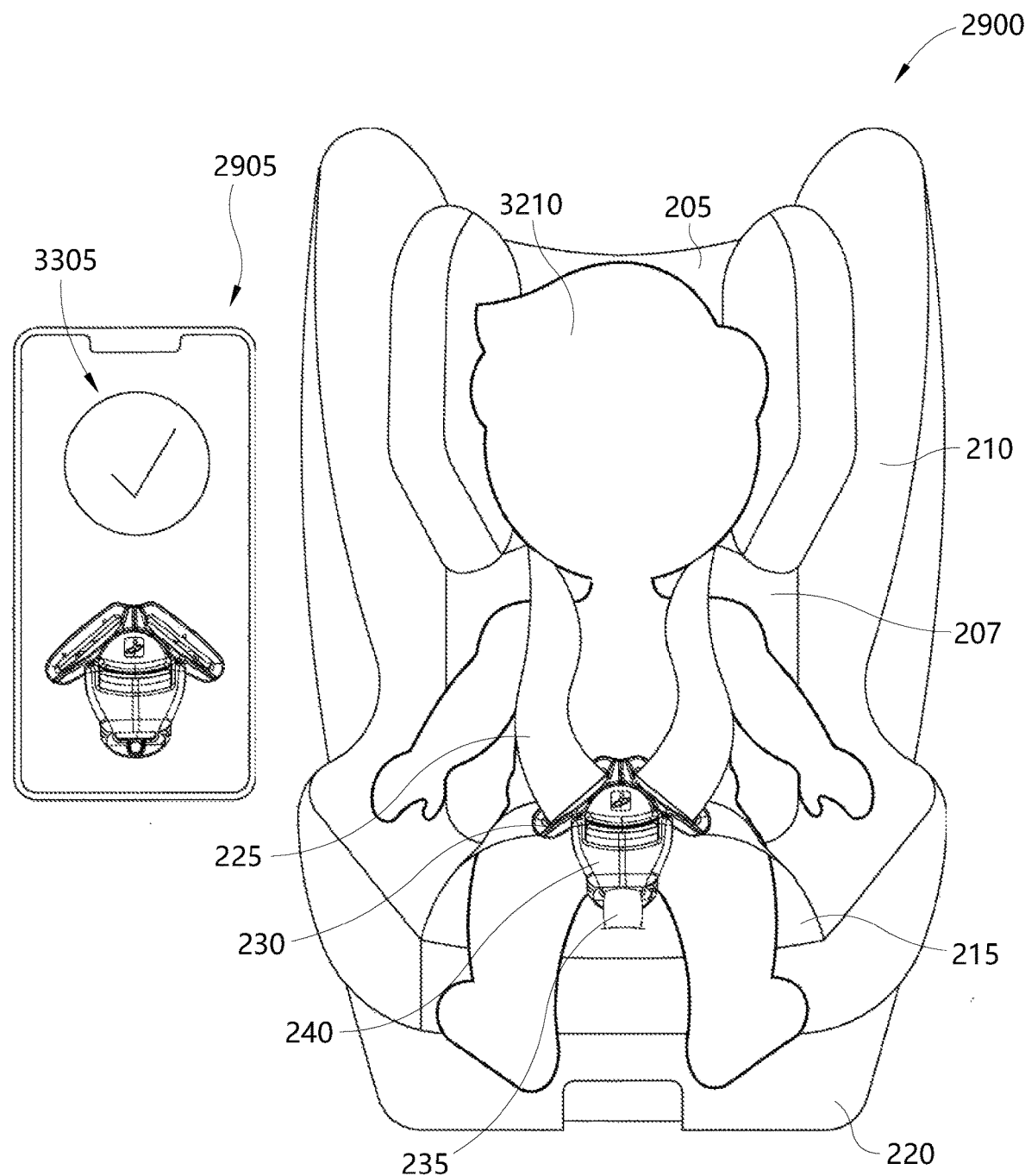
FIG. 33 is a front view of the child safety seat of FIG. 29.

At FIG. 32, the mobile device 2905 displays a third status indicator 3205. The third status indicator 3205 shows a photo of a child including a positive mark and/or a checkmark. The third status indicator 3205 indicates that the occupant sensor 130 detects a child 3210 within the child safety seat 2900. The third status indicator 3205 may display a red X and/or other negative indicator If the child 3210 is not within the child safety seat 2900. In FIG. 33, the mobile device 2905 depicts a fourth status indicator 3305. The fourth status indicator 3305 shows a photo of the latch plates 230 and buckle 240 as well as a positive indicator and/or checkmark. The fourth status indicator 3305 indicates that the latch plates 230 and buckle 240 are properly buckled. The fourth status indicator 3305 may display a red X and/or other negative indicator if the latch plates 230 and the buckle 240 are not properly buckled.

Figure 34:
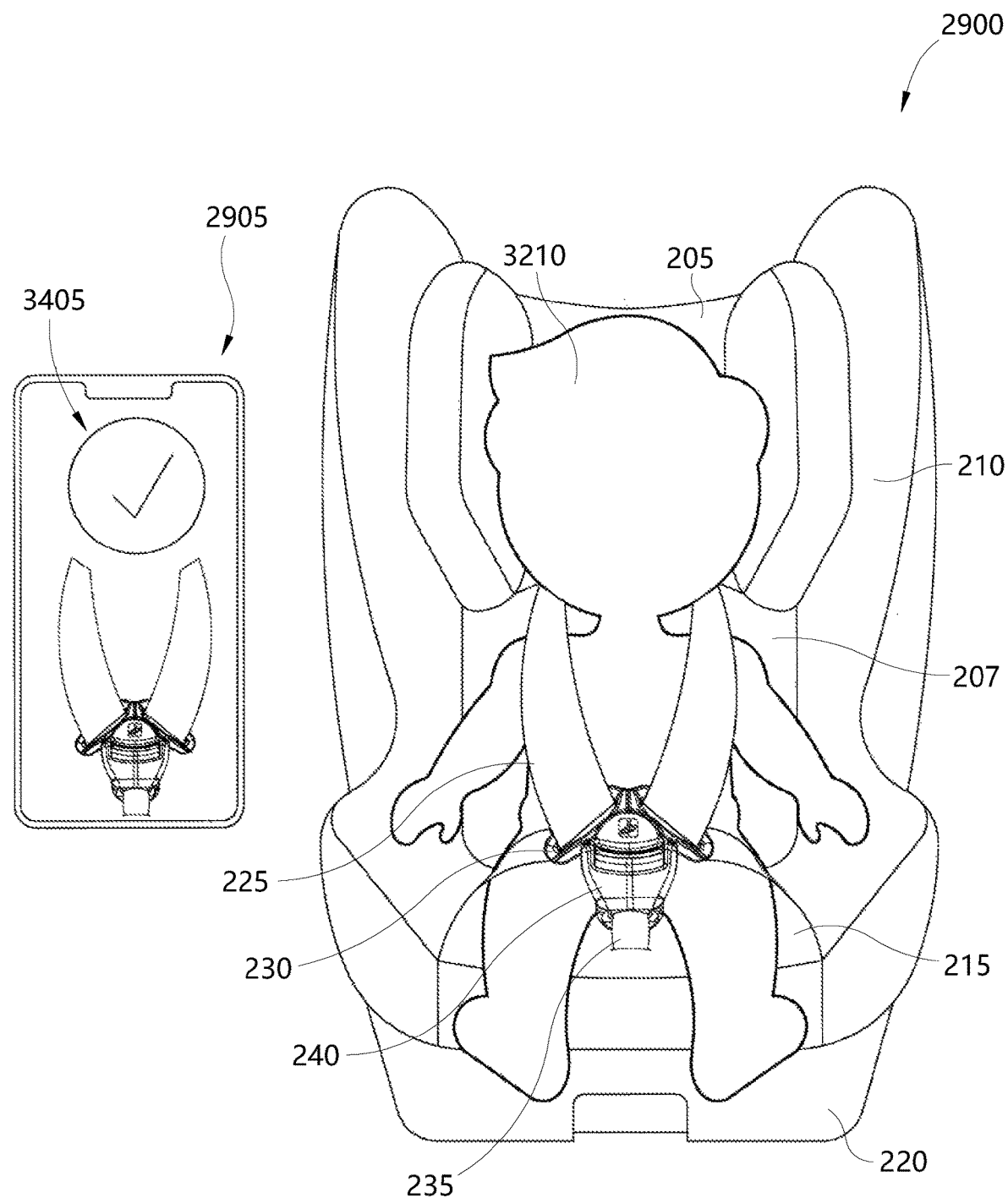
FIG. 34 is a front view of the child safety seat of FIG. 29.
Figure 35:
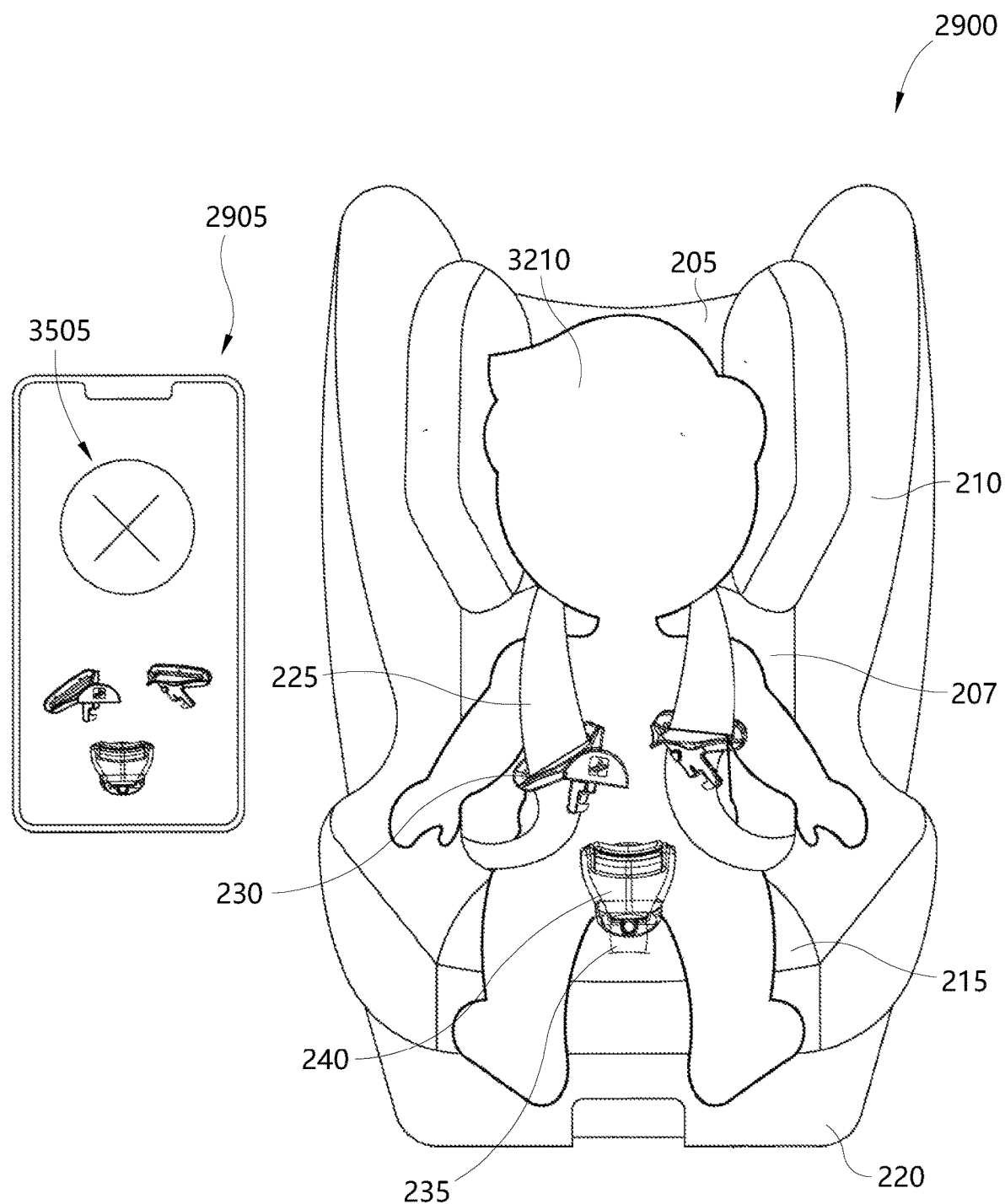
FIG. 35 is a front view of the child safety seat of FIG. 29.

In FIG. 34, the mobile device 2905 displays a fifth status indicator 3405. The fifth status indicator 3405 shows a photo of the shoulder belts 225 and buckle belt 235 as well as a checkmark and/or other positive indicator. The fifth status indicator 3405 indicates that the shoulder belts 225 and the buckle belt 235 of the harness 222 are properly tensioned. The fifth status indicator 3405 may display a red X and/or other negative indicator if the harness 222 is not properly tensioned. Additionally, the processor 105 commands the motors 145 to tension the harness 222 to the required specifications. At FIG. 35, the mobile device 2905 depicts a sixth status indicator 3505. The sixth status indicator 3505 shows a photo of the latch plates 230 and buckle 240 along with a red "X" and/or other negative image. The sixth status indicator 3505 indicates that the latch plates 230 and buckle 240 are not buckled. When the latch plates 230 and buckle 240 are unbuckled, the motor 145 loosens the harness 222 and the child safety seat 2900 returns to the dormant state.

Glossary of Terms

The language used in the claims and specification is to only have its plain and ordinary meaning, except as explicitly defined below. The words in these definitions are to only have their plain and ordinary meaning. Such plain and ordinary meaning is inclusive of all consistent dictionary definitions from the most recently published Webster's dictionaries and Random House dictionaries. As used in the specification and claims, the following definitions apply to these terms and common variations thereof identified below.

"About" with reference to numerical values generally refers to plus or minus 10% of the stated value. For example if the stated value is 4.375, then use of the term "about 4.375" generally means a range between 3.9375 and 4.8125.

"Accelerometer" generally refers to a device or instrument that measures acceleration or the rate of change of velocity. In one form, the accelerometer measures proper acceleration in which the acceleration of a body relative to the instantaneous rest frame of the body. The accelerometer can include single-axis or multi-axis type accelerometers. By way of non-limiting examples, the accelerometer can include capacitive, resistive, capacitive, servo, laser, magnetic induction, optical, piezoelectric, resonance, and quantum type accelerometers, just to name a few.

"Aftermarket Product" generally refers to one or more parts and/or accessories used in repair and/or enhancement of a product already made and sold by an Original Equipment Manufacturer (OEM). For example, aftermarket products can include spare parts, accessories, and/or components for motor vehicles.

"And/Or" generally refers to a grammatical conjunction indicating that one or more of the cases it connects may occur. For instance, it can indicate that either or both of two stated cases can occur. In general, "and/or" includes any combination of the listed collection. For example, "X, Y, and/or Z" encompasses: any one letter individually (e.g., {X}, {Y}, {Z}); any combination of two of the letters (e.g., {X, Y}, {X, Z}, {Y, Z}); and all three letters (e.g., {X, Y, Z}). Such combinations may include other unlisted elements as well.

"Buckle" generally refers to device, such as in the form of a clasp, that releasably secures two or more loose ends together. Typically, but not always one end is secured to or otherwise attached to the clasp device, and the other end is releasably or adjustably held by the clasp device. The ends can be for a variety of objects such as straps, belts, cables, and webbing, to name just a few. One common type of buckle is a seat belt buckle found in a wide variety of vehicles. For instance, the buckle can be used in two-point, three-point, four-point, five-point, or six-point harness systems. In one example, the loose end of a seat belt is looped through a slot in a latch plate that includes a tongue, and to secure the loose end, the tongue is inserted into a seat belt buckle that is attached to a fixed seat belt or webbing.

"Child Safety Seat", "Car Seat", or "Child Restraint System" generally refer to a seat that is specifically designed to protect children from injury during a vehicle collision. Commonly, the child safety seat is an aftermarket product that is installed by an owner into a vehicle after purchase of the vehicle, but the child safety seat can be also integrated into a seat of the vehicle by a manufacturer of the vehicle. In contrast to most vehicle seats, which are designed to accommodate adults, the child safety seat is sized and configured to properly position a child or infant to reduce injury during an accident. The child safety further typically includes a passive restraint system, such as a harness, that generally hold an occupant of the seat in place during a collision. The restraint system for example can include a five-point harness, but other types of harnesses and restraints can be used. When sold as a separate, aftermarket product, the child safety seat can include an anchoring mechanism, like an Isofix connecter, configured to secure the child safety seat to the vehicle (e.g., via an Isofix anchor in the vehicle). Some typical types of child safety seats include infant seats, convertible seats, combination seats, and booster seats, just to name a few.

"Communication Link" or "Communication Channel" generally refers to a connection between two or more communicating entities and may or may not include a communications channel between the communicating entities. The communication between the communicating entities may occur by any suitable means. For example, the connection may be implemented as an actual physical link, an electrical link, an electromagnetic link, a logical link, or any other suitable linkage facilitating communication. In the case of an actual physical link, communication may occur by multiple components in the communication link configured to respond to one another by physical movement of one element in relation to another. In the case of an electrical link, the communication link may be composed of multiple electrical conductors electrically connected to form the communication link. In the case of an electromagnetic link, elements of the connection may be implemented by sending or receiving electromagnetic energy at any suitable frequency, thus allowing communications to pass as electromagnetic waves. These electromagnetic waves may or may not pass through a physical medium such as an optical fiber, or through free space, or any combination thereof. Electromagnetic waves may be passed at any suitable frequency including any frequency in the electromagnetic spectrum. In the case of a logical link, the communication links may be a conceptual linkage between the sender and recipient such as a transmission station in the receiving station. Logical link may include any combination of physical, electrical, electromagnetic, or other types of communication links.

"Controller" generally refers to a device, using mechanical, hydraulic, pneumatic electronic techniques, and/or a microprocessor or computer, which monitors and physically alters the operating conditions of a given dynamical system. In one non-limiting example, the controller can include an Allen Bradley brand Programmable Logic Controller (PLC). A controller may include a processor for performing calculations to process input or output. A controller may include a memory for storing values to be processed by the processor, or for storing the results of previous processing. A controller may also be configured to accept input and output from a wide array of input and output devices for receiving or sending values. Such devices include other computers, keyboards, mice, visual displays, printers, industrial equipment, and systems or machinery of all types and sizes. For example, a controller can control a network or network interface to perform various network communications upon request. The network interface may be part of the controller, or characterized as separate and remote from the controller. A controller may be a single, physical, computing device such as a desktop computer, or a laptop computer, or may be composed of multiple devices of the same type such as a group of servers operating as one device in a networked cluster, or a heterogeneous combination of different computing devices operating as one controller and linked together by a communication network. The communication network connected to the controller may also be connected to a wider network such as the Internet. Thus, a controller may include one or more physical processors or other computing devices or circuitry, and may also include any suitable type of memory. A controller may also be a virtual computing platform having an unknown or fluctuating number of physical processors and memories or memory devices. A controller may thus be physically located in one geographical location or physically spread across several widely scattered locations with multiple processors linked together by a communication network to operate as a single controller. Multiple controllers or computing devices may be configured to communicate with one another or with other devices over wired or wireless communication links to form a network. Network communications may pass through various controllers operating as network appliances such as switches, routers, firewalls or other network devices or interfaces before passing over other larger computer networks such as the Internet. Communications can also be passed over the network as wireless data transmissions carried over electromagnetic waves through transmission lines or free space. Such communications include using WiFi or other Wireless Local Area Network (WLAN) or a cellular transmitter/receiver to transfer data.

"Display" or "Display Device" generally refers to any device capable of being controlled by an electronic circuit or processor to display information in a visual or tactile manner. A display device may be configured as an input device taking input from a user or other system (e.g. a touch sensitive computer screen), or as an output device generating visual or tactile information, or the display device may be configured to operate as both an input or output device at the same time, or at different times. The output may be two-dimensional, three-dimensional, and/or mechanical displays and includes, but is not limited to, the following display technologies: Cathode Ray Tube display (CRT), Light-Emitting Diode display (LED), Electroluminescent Display (ELD), electronic paper, Electrophoretic Ink (E-ink), Plasma Display Panel (PDP), Liquid Crystal Display (LCD), High-Performance Addressing display (HPA), Thin-film Transistor display (TFT), Organic Light-Emitting Diode display (OLED), Surface-conduction Electron-emitter Display (SED), laser TV, carbon nanotubes, quantum dot display, Interferometric Modulator Display (IMOD), Swept-volume display, Varifocal mirror display, Emissive volume display, Laser display, Holographic display, Light field displays, Volumetric display, Ticker tape, Split-flap display, Flip-disc display (or flip-dot display), Rollsign, mechanical gauges with moving needles and accompanying indicia, Tactile electronic displays (aka refreshable Braille display), Optacon displays, or any devices that either alone or in combination are configured to provide visual feedback on the status of a system, such as the "check engine" light, a "low altitude" warning light, and/or an array of red, yellow, and green indicators configured to indicate a temperature range.

"Electric Motor" generally refers to an electrical machine that converts electrical energy into mechanical energy. Normally, but not always, electric motors operate through the interaction between one or more magnetic fields in the motor and winding currents to generate force in the form of rotation. Electric motors can be powered by direct current (DC) sources, such as from batteries, motor vehicles, and/or rectifiers, or by alternating current (AC) sources, such as a power grid, inverters, and/or electrical generators. An electric generator can (but not always) be mechanically identical to an electric motor, but operates in the reverse direction, accepting mechanical energy and converting the mechanical energy into electrical energy.

"Electrically Connected" generally refers to a configuration of two objects that allows electricity to flow between them or through them. In one example, two conductive materials are physically adjacent one another and are sufficiently close together so that electricity can pass between them. In another example, two conductive materials are in physical contact allowing electricity to flow between them.

"Electronic Control Unit (ECU)" or "Electronic Control Module (ECM)" generally refers to an embedded system in electronics of a vehicle that controls one or more electrical systems and/or subsystems of the vehicle. Usually, but not always, ECUs communicate over a Controller Area Network (CAN) and can act as nodes over the CAN. The complexity of the ECU or node can range from a simple Input/Output (I/O) device up to an embedded computer with a CAN interface and software. The ECU or node can also act as a gateway allowing a general purpose computer to communicate over an interface, such as via a USB and/or Ethernet port, to the devices on the CAN network. Each ECU usually, but not always, includes a central processing unit, a CAN controller, and a transceiver. These ECUs can for instance include Engine Control Modules (ECMs) and Transmission Control Modules (TCMs) as well as other control units such as for airbags, antilock braking/ABS, cruise control, electric power steering, audio systems, power windows, doors, mirror adjustment, battery and/or hybrid/electric recharging systems, to name just a few. By way of nonlimiting examples, types of ECUs can include ECMs, TCMs, Powertrain Control Module (PCMs), Brake Control Modules (BCMs or EBCMs), Central Control Modules (CCMs), Central Timing Modules (CTMs), General Electronic Modules (GEMs), Body Control Modules (BCMs), and/or Suspension Control Modules (SCMs), to name just a few.

"Energy Source" generally refers to a device, structure, mechanism, and/or system that provides power for performing work. The energy supplied by the energy source can take many forms including electrical, chemical, electrochemical, nuclear, hydraulic, pneumatic, gravitational, kinetic, and/or potential energy forms. The energy source for instance can include ambient energy sources, such as solar panels, external energy sources, such as from electrical power transmission networks, and/or portable energy sources, such as batteries. The energy source can include an energy carrier containing energy that can be later converted to other forms, such as into mechanical, heat, electrical, and/or chemical forms. Energy carriers can for instance include springs, electrical batteries, capacitors, pressurized air, dammed water, hydrogen, petroleum, coal, wood, and/or natural gas, to name just a few.

"Fastener" generally refers to a hardware device that mechanically joins or otherwise affixes two or more objects together. By way of non-limiting examples, the fastener can include bolts, dowels, nails, nuts, pegs, pins, rivets, screws, buttons, hook and loop fasteners, and snap fasteners, to just name a few.

"Five-Point Harness" generally refers to a restraint system that includes five straps or web portions that are mounted to a seat. Two of the straps are typically located to secure at the shoulders of an occupant of the seat, and another two of the straps are typically located proximal the hips of the occupant when seated. One of the straps is located at the crotch of the occupant when seated in the seat, and this strap typically includes a releasable buckle or other similar mechanism that releasable secures the five straps together so as to secure the occupant in the seat. The straps can be tightened or loosened depending on the size of the occupant and/or whether the occupant is being secured or removed from the seat. Five-point harnesses can be for example integrated into race car seats or child safety seats.

"Harness" generally refers to a set of straps and fittings for fastening a human or other animal in a particular place and/or position. The straps can come on many forms, such as belts, webbing, or ropes, and the straps can be made of a variety of materials such as natural or synthetic materials. The fittings are designed in a variety of forms for securing the straps around the individual as well as releasing the straps to free the individual. The harness can include webbing, buckles, latch plates, and/or length-adjustment mechanisms, such as a retractor. In one example, the fitting includes a set of latch plates that are secured in a buckle release mechanism. Harnesses can for instance be integrated into vehicle seats, child booster seats, and child safety seats. The straps and fitting can be configured in a number of manners such as to form three-point, five-point, and six-point harnesses, to name just a few examples.

"Headrest" or "Head Restraint" generally refers to a structure attached or otherwise integrated into the top of a seat to limit the rearward movement of the head of the seat occupant, relative to the torso, in a collision. For instance, the headrest is designed to prevent or mitigate whiplash or other injury to the cervical vertebrae. The headrest can include a fixed headrest or an adjustable headrest. The adjustable headrest is capable of being positioned to fit the morphology of the seated occupant. The adjustable headrest can be adjusted manually and/or automatically. Another type of headrest includes an active head restraint designed to automatically improve head restraint position and/or geometry for the seat occupant during a collision.

"Input Device" generally refers to any device coupled to a computer that is configured to receive input and deliver the input to a processor, memory, or other part of the computer. Such input devices can include keyboards, mice, trackballs, and touch sensitive pointing devices such as touchpads or touchscreens. Input devices also include any sensor or sensor array for detecting environmental conditions such as temperature, light, noise, vibration, humidity, and the like.

"Input/Output (I/O) Device" generally refers to any device or collection of devices coupled to a computing device that is configured to receive input and deliver the input to a processor, memory, or other part of the computing device and/or is controlled by the computing device to produce an output. The I/O device can include physically separate input and output devices, or the input and output devices can be combined together to form a single physical unit. Such input devices of the I/O device can include keyboards, mice, trackballs, and touch sensitive pointing devices such as touchpads or touchscreens. Input devices also include any sensor or sensor array for detecting environmental conditions such as temperature, light, noise, vibration, humidity, and the like. Examples of output devices for the I/O device include, but are not limited to, screens or monitors displaying graphical output, a projecting device projecting a two-dimensional or three-dimensional image, or any kind of printer, plotter, or similar device producing either two-dimensional or three-dimensional representations of the output fixed in any tangible medium (e.g., a laser printer printing on paper, a lathe controlled to machine a piece of metal, or a three-dimensional printer producing an object). An output device may also produce intangible output such as, for example, data stored in a database, or electromagnetic energy transmitted through a medium or through free space such as audio produced by a speaker controlled by the computer, radio signals transmitted through free space, or pulses of light passing through a fiber-optic cable.

"Isofix" or "ISOFIX" generally refers to an international standard for attachment points for child safety seats in passenger cars and other vehicles and/or attachment point or anchoring systems that satisfy the standard. More specifically, Isofix refers International Organization for Standardization (ISO) standard ISO 13216, which specifies the anchoring system for Group 1 child safety seats. This standard defines standard attachment points to be manufactured into cars, enabling compliant child safety seats to be quickly and safely secured. Isofix acts as an alternative to securing the seat with seat belts. In one form, child safety seats are secured with a single attachment at the top (e.g., top tether) and two attachments at the base of each side of the seat. The Isofix standard can be identified by other regional names. In the United States for example, the standard is commonly referred to as a LATCH ("Lower Anchors and Tethers for Children") system.

"Latch Plate" generally refers to a part of a vehicle belt assembly that releasably connects to a buckle and through which the webbing is threaded or otherwise secured. Typically, but not always, the latch plate is in at least part made of metal and/or plastic. The latch plate includes one or more tongues that are inserted into the buckle. Each tongue can include a notch or other opening that is used to secure the latch plate to the buckle. By way of non-limiting examples, the latch plates can include free-sliding latch plates, cinching latch plates, locking latch plates, and switchable latch plates, to name just a few examples.

"Light Emitting Diode" or "LED" generally refers to a semiconductor diode, made from certain materials, in which light is emitted in response to application of an electrical current. A variety of materials in the LED can produce a range of colors. The color of the light (corresponding to the energy of the photons) is determined by the energy required for electrons to cross the band gap of the semiconductor. Typically, but not always, white light is obtained by using multiple semiconductors or a layer of light-emitting phosphor on the semiconductor device. The LED can come in the form of a variety of colors, shapes, sizes and designs, including with or without heat sinking, lenses, or reflectors, built into the package.

"Memory" generally refers to any storage system or device configured to retain data or information. Each memory may include one or more types of solid-state electronic memory, magnetic memory, or optical memory, just to name a few. Memory may use any suitable storage technology, or combination of storage technologies, and may be volatile, nonvolatile, or a hybrid combination of volatile and nonvolatile varieties. By way of non-limiting example, each memory may include solid-state electronic Random Access Memory (RAM), Sequentially Accessible Memory (SAM) (such as the First-In, First-Out (FIFO) variety or the Last-In-First-Out (LIFO) variety), Programmable Read Only Memory (PROM), Electronically Programmable Read Only Memory (EPROM), or Electrically Erasable Programmable Read Only Memory (EEPROM).

Memory can refer to Dynamic Random Access Memory (DRAM) or any variants, including Static Random Access Memory (SRAM), Burst SRAM or Synch Burst SRAM (BSRAM), Fast Page Mode DRAM (FPM DRAM), Enhanced DRAM (EDRAM), Extended Data Output RAM (EDO RAM), Extended Data Output DRAM (EDO DRAM), Burst Extended Data Output DRAM (BEDO DRAM), Single Data Rate Synchronous DRAM (SDR SDRAM), Double Data Rate SDRAM (DDR SDRAM), Direct Rambus DRAM (DRDRAM), or Extreme Data Rate DRAM (XDR DRAM).

Memory can also refer to non-volatile storage technologies such as Non-Volatile Read Access memory (NVRAM), flash memory, non-volatile Static RAM (nvSRAM), Ferroelectric RAM (FeRAM), Magnetoresistive RAM (MRAM), Phase-change RAM (PRAM), Conductive-Bridging RAM (CBRAM), Silicon-Oxide-Nitride-Oxide-Silicon (SONOS), Resistive RAM (RRAM), Domain Wall Memory (DWM) or "Racetrack" memory, Nano-RAM (NRAM), or Millipede memory. Other non-volatile types of memory include optical disc memory (such as a DVD or CD ROM), a magnetically encoded hard disc or hard disc platter, floppy disc, tape, or cartridge media. The concept of a "memory" includes the use of any suitable storage technology or any combination of storage technologies.

"Motor" generally refers to a machine that supplies motive power for a device with moving parts. The motor can include rotor and linear type motors. The motor can be powered in any number of ways, such as via electricity, internal combustion, pneumatics, and/or hydraulic power sources. By way of non-limiting examples, the motor can include a servomotor, a pneumatic motor, a hydraulic motor, a steam engine, a pneumatic piston, a hydraulic piston, and/or an internal combustion engine.

"Output Device" generally refers to any device or collection of devices that is controlled by computer to produce an output. This includes any system, apparatus, or equipment receiving signals from a computer to control the device to generate or create some type of output. Examples of output devices include, but are not limited to, screens or monitors displaying graphical output, any projecting device projecting a two-dimensional or three-dimensional image, any kind of printer, plotter, or similar device producing either two-dimensional or three-dimensional representations of the output fixed in any tangible medium (e.g. a laser printer printing on paper, a lathe controlled to machine a piece of metal, or a three-dimensional printer producing an object). An output device may also produce intangible output such as, for example, data stored in a database, or electromagnetic energy transmitted through a medium or through free space such as audio produced by a speaker controlled by the computer, radio signals transmitted through free space, or pulses of light passing through a fiber-optic cable.

"Pressure Sensor" generally refers to a device for pressure measurement of fluids, such as gases and/or liquids. Generally, the pressure sensor usually acts as a transducer by generating a signal as a function of the pressure imposed on the sensor. When the pressure sensor is an electronic type sensor, the generated signal can include an analog or digital signal. The pressure sensor can for example measure or detect pressure relative to a perfect vacuum, atmospheric pressure, a fixed pressure value, or a differential pressure value. By way of non-limiting examples, pressure sensors can include absolute, gauge, vacuum, differential, and sealed type pressure sensors. The pressure sensor can detect the pressure in a wide variety of ways, such as through capacitive, electromagnetic, piezoelectric, strain-gauge, optical, potentiometric, resonant frequency, thermal, and/or ionization techniques, to name just a few.

"Processor" generally refers to one or more electronic components configured to operate as a single unit configured or programmed to process input to generate an output. Alternatively, when of a multi-component form, a processor may have one or more components located remotely relative to the others. One or more components of each processor may be of the electronic variety defining digital circuitry, analog circuitry, or both. In one example, each processor is of a conventional, integrated circuit microprocessor arrangement, such as one or more PENTIUM, i3, i5 or i7 processors supplied by INTEL Corporation of 2200 Mission College Boulevard, Santa Clara, Calif. 95052, USA. In another example, the processor uses a Reduced Instruction Set Computing (RISC) architecture, such as an Advanced RISC Machine (ARM) type processor developed and licensed by ARM Holdings of Cambridge, United Kingdom. In still yet other examples, the processor can include a Central Processing Unit (CPU) and/or an Accelerated Processing Unit (APU), such as those using a K8, K10, Bulldozer, Bobcat, Jaguar, and Zen series architectures, supplied by Advanced Micro Devices, Inc. (AMD) of Santa Clara, Calif. Another example of a processor is an Application-Specific Integrated Circuit (ASIC). An ASIC is an Integrated Circuit (IC) customized to perform a specific series of logical operations for controlling the computer to perform specific tasks or functions. An ASIC is an example of a processor for a special purpose computer, rather than a processor configured for general-purpose use. An application-specific integrated circuit generally is not reprogrammable to perform other functions and may be programmed once when it is manufactured. In another example, a processor may be of the "field programmable" type. Such processors may be programmed multiple times "in the field" to perform various specialized or general functions after they are manufactured. A field-programmable processor may include a Field-Programmable Gate Array (FPGA) in an integrated circuit in the processor. An FPGA may be programmed to perform a specific series of instructions which may be retained in nonvolatile memory cells in the FPGA. The FPGA may be configured by a customer or a designer using a Hardware Description Language (HDL). An FPGA may be reprogrammed using another computer to reconfigure the FPGA to implement a new set of commands or operating instructions. Such an operation may be executed in any suitable means such as by a firmware upgrade to the processor circuitry. Just as the concept of a computer is not limited to a single physical device in a single location, so also the concept of a "processor" is not limited to a single physical logic circuit or package of circuits but includes one or more such circuits or circuit packages possibly contained within or across multiple computers in numerous physical locations. In a virtual computing environment, an unknown number of physical processors may be actively processing data, and the unknown number may automatically change over time as well. The concept of a "processor" includes a device configured or programmed to make threshold comparisons, rules comparisons, calculations, or perform logical operations applying a rule to data yielding a logical result (e.g. "true" or "false"). Processing activities may occur in multiple single processors on separate servers, on multiple processors in a single server with separate processors, or on multiple processors physically remote from one another in separate computing devices.

"Seat" generally refers to a type of support structure or a place constructed for the purpose of allowing a human and/or other animal to sit. Some examples of seats include chairs, stools, benches, saddles, and sofas to name just a few. Typically, but not always, the seat can further include a backrest, armrest, and a headrest as well as other features.

"Seat Belt", "Safety Belt", "Vehicle Belt", or "Belt" generally refers to an arrangement of webs, straps, and other devices designed to restrain or otherwise hold a person or other object steady such as in a boat, vehicle, aircraft, and/or spacecraft. For example, the seat belt is designed to secure an occupant of a vehicle against harmful movement that may result during a collision or a sudden stop. By way of non-limiting examples, the seat belt can include webbing, buckles, latch plates, and/or length-adjustment mechanisms, such as a retractor, installed in the vehicle that is used to restrain an occupant or a child restraint system. The seat belt for instance can include a lap belt only, a combination lap-shoulder belt, a separate lap belt, a separate shoulder belt, and/or a knee bolster.

"Sensor" generally refers to an object whose purpose is to detect events and/or changes in the environment of the sensor, and then provide a corresponding output. Sensors include transducers that provide various types of output, such as electrical and/or optical signals. By way of nonlimiting examples, the sensors can include pressure sensors, ultrasonic sensors, humidity sensors, gas sensors, motion sensors, acceleration sensors, displacement sensors, force sensors, optical sensors, and/or electromagnetic sensors. In some examples, the sensors include barcode readers, RFID readers, and/or vision systems. In other examples, the sensor includes an encoder configured to detect and encode rotational movement. The sensor may be a conductive encoder, an optical encoder, an on-axis magnetic encoder, and/or an off-axis magnetic encoder. In some forms, the sensor can be configured to convert the rotation of the encoder gear to an output signal. The output signal can be digital or analog. The output signal of the sensor indicates the position of the encoder gear.

"Shoulder" generally refers to a combination of three separate bones. In humans, the bones making up the shoulder include the clavicle, the scapula, and the humerus. Generally, the shoulder is located where the arm meets the torso on a human. In other examples, the shoulders define the width of a human with the outer edges of the shoulders being the widest part.

"Transceiver" generally refers to a device that includes both a transmitter and a receiver that share common circuitry and/or a single housing. Transceivers are typically, but not always, designed to transmit and receive electronic signals, such as analog and/or digital radio signals.

"Vehicle" generally refers to a machine that transports people and/or cargo. Common vehicle types can include land-based vehicles, amphibious vehicles, watercraft, aircraft, and space craft. By way of non-limiting examples, land-based vehicles can include wagons, carts, scooters, bicycles, motorcycles, automobiles, buses, trucks, semi-trailers, trains, trolleys, and trams. Amphibious vehicles can for example include hovercraft and duck boats, and watercraft can include ships, boats, and submarines, to name just a few examples. Common forms of aircraft include airplanes, helicopters, autogiros, and balloons, and spacecraft for instance can include rockets and rocket powered aircraft. The vehicle can have numerous types of power sources. For instance, the vehicle can be powered via human propulsion, electrically powered, powered via chemical combustion, nuclear powered, and/or solar powered. The direction, velocity, and operation of the vehicle can be human controlled, autonomously controlled, and/or semi-autonomously controlled. Examples of autonomously or semi-autonomously controlled vehicles include Automated Guided Vehicles (AGVs) and drones.

"Waist" generally refers to a component of the body located between the bottom of the rib cage and the pelvis. In some examples, the waist includes the hips. Generally, the waist is defined as being a narrower middle part of the body. In other examples, the waist is the area of the body around which pants generally fasten.

"Web" or "Webbing" generally refers to a strap made of a network of thread, strings, cords, wires, and/or other materials designed to restrain or otherwise hold a person or other object steady such as in a boat, vehicle, aircraft, and/or spacecraft. By way of non-limiting examples, the web can be incorporated into a seat belt, a child booster seat, and/or a car seat.

It should be noted that the singular forms "a," "an," "the," and the like as used in the description and/or the claims include the plural forms unless expressly discussed otherwise. For example, if the specification and/or claims refer to "a device" or "the device", it includes one or more of such devices.

It should be noted that directional terms, such as "up," "down," "top," "bottom," "lateral," "longitudinal," "radial," "circumferential," "horizontal," "vertical," etc., are used herein solely for the convenience of the reader in order to aid in the reader's understanding of the illustrated embodiments, and it is not the intent that the use of these directional terms in any manner limit the described, illustrated, and/or claimed features to a specific direction and/or orientation.

While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the inventions defined by the following claims are desired to be protected. All publications, patents, and patent applications cited in this specification are herein incorporated by reference as if each individual publication, patent, or patent application were specifically and individually indicated to be incorporated by reference and set forth in its entirety herein.

| Reference Numbers |
|---|
| 100 seat monitoring system |
| 105 processor |
| 110 memory |
| 115 transceiver |
| 120 I/O device |
| 125 headrest position sensor |
| 130 occupant sensor |
| 135 buckle sensor |
| 140 tension sensor |
| 145 motor |
| 200 child safety seat |
| 205 headrest |
| 207 seat back |
| 209 arrow |
| 210 seat body |
| 215 seat bottom |
| 220 seat base |
| 222 harness |
| 225 shoulder belts |
| 230 latch plates |
| 235 buckle belt |
| 240 buckle |
| 245 shoulder belt tension sensor |
| 250 buckle belt tension sensor |
| 300 interior portion |
| 505 base |
| 510 cover |
| 512 wires |
| 515 positive signal wire |
| 520 negative signal wire |
| 525 positive power wire |
| 530 negative power wire |
| 605 actuator |
| 610 plunger |
| 615 foil actuator |
| 705 positive signal mounting location |
| 710 negative signal mounting location |
| 715 foil |
| 805 headrest sensor assembly |
| 810 arrow |
| 900 back side |
| 905 lowered position |
| 1005 raised position |
| 1105 guides |
| 1110 adjustable rail |
| 1111 first end |
| 1114 second end |

| Reference Numbers |
|---|
| 1115 tape |
| 1120 rotary sensor |
| 1125 fastener |
| 1130 arrow |
| 1135 arrow |
| 1205 brace |
| 1305 body |
| 1310 base |
| 1315 apertures |
| 1320 axle |
| 1322 arbor |
| 1325 spool |
| 1330 inner flange |
| 1335 outer flange |
| 1340 barrel |
| 1345 slot |
| 1400 flowchart |
| 1405 stage |
| 1410 stage |
| 1415 stage |
| 1420 stage |
| 1425 stage |
| 1430 stage |
| 1435 stage |
| 1500 flowchart |
| 1505 stage |
| 1510 stage |
| 1515 stage |
| 1520 stage |
| 1525 stage |
| 1530 stage |
| 1535 stage |
| 1540 stage |
| 1545 stage |
| 1550 stage |
| 1555 stage |
| 1560 stage |
| 1565 stage |
| 1600 child safety seat |
| 1605 indicator system |
| 1610 light emitting diode |
| 1705 first LED |
| 1805 second LED |
| 1810 child |
| 1905 third LED |
| 2005 fourth LED |
| 2200 child safety seat |
| 2205 display |
| 2305 first status indicator |
| 2405 second status indicator |
| 2505 third status indicator |
| 2510 child |
| 2605 fourth status indicator |
| 2705 fifth status indicator |
| 2805 sixth status indicator |
| 2900 child safety seat |
| 2905 mobile device |
| 3005 first status indicator |
| 3105 second status indicator |
| 3205 third status indicator |
| 3210 child |
| 3305 fourth status indicator |
| 3405 fifth status indicator |
| 3505 sixth status indicator |

What is claimed is:

1. A system, comprising:
a seat monitoring system configured to monitor status of a child safety seat;
wherein the seat monitoring system includes one or more sensors configured to sense the status of the child safety seat;
wherein the seat monitoring system includes an output device to provide the status of the child safety seat;

wherein the sensors include a headrest position sensor configured to determine position of the headrest of the child safety seat;
wherein the headrest position sensor includes a rotary sensor;
wherein the headrest position sensor includes a tape coupled to the headrest and the rotary sensor;
wherein the rotary sensor includes a spool;
wherein the tape is wrapped around the spool of the rotary sensor; and
wherein a length of the tape unspooled from the spool corresponds to position of the headrest.

2. The system of claim 1, wherein the output device is configured to provide an indicator of the position of the headrest.

3. The system of claim 1, wherein:
the seat monitoring system includes a processor; and
the output device is configured to display a negative indicator when the position of the headrest is different from a specified position.

4. The system of claim 1, wherein the sensors include a buckle sensor configured to sense buckling status of a buckle of a harness of the child safety seat.

5. The system of claim 1, wherein the sensors include one or more tension sensors configured to sense tension of a harness of the child safety seat.

6. The system of claim 5, wherein the tension sensors include one or more shoulder belt tension sensors, and the shoulder belt tension sensors are configured to measure tension of one or more shoulder belts of the harness.

7. The system of claim 5, wherein the tension sensors include a buckle belt tension sensor, and the buckle belt tension sensor is configured to measure tension applied to a buckle belt of the harness of the child safety seat.

8. The system of claim 5, wherein the tension sensors include one or more strain gauges.

9. The system of claim 5, wherein the seat monitoring system is configured to automatically adjust tension of the harness based at least on tension data from the tension sensors.

10. The system of claim 9, wherein the seat monitoring system includes a motor configured to adjust the tension of the harness.

11. The system of claim 10, wherein:
the sensor includes an occupancy sensor configured to determine if an occupant is sitting in the child safety seat;
the sensors include a buckle sensor configured to sense buckling status of the buckle of the harness;
the motor is configured to tighten the harness when the buckle is buckled and the occupancy sensor detects an occupant; and
the motor is configured to loosen the harness when the buckle is unbuckled.

12. The system of claim 1, further comprising:
an input device configured to receive user inputs concerning biometric information about an occupant of the child safety seat.

13. The system of claim 1, further comprising the child safety seat.

14. The system of claim 13, wherein the child safety seat includes
a seat back,
a headrest, wherein the headrest is configured to move relative to the seat back,
a seat bottom extending outward from the seat back,
a harness,
wherein the harness includes a buckle,
wherein the harness includes one or more belts,
wherein the belts include a buckle belt,
wherein the buckle belt coupled to the buckle,
wherein the belts include one or more shoulder belts, and
wherein the shoulder belts extend from the seat back to the seat bottom.

15. A method of operating a child safety seat, comprising:
measuring a position of a headrest of the child safety seat with a headrest position sensor of a seat monitoring system;
determining that the child safety seat is occupied with an occupancy sensor of the seat monitoring system;
determining with the seat monitoring system that the position of the headrest satisfies headrest specifications for an occupant;
sensing tension of one or more belts of a harness with one or more tension sensors of the seat monitoring system;
detecting buckling of a buckle of the harness with a buckle sensor of the seat monitoring system; and
tightening the belts of the harness until proper tension is reached.

16. The method of claim 15, further comprising:
detecting unbuckling of a buckle with the buckle sensor of the seat monitoring system; and
loosening the belts of the harness in response to the detecting unbuckling.

17. The method of claim 16, wherein the loosening the belts includes releasing tension applied to the belts by a motor.

18. The method of claim 15, further comprising:
determining a specified position for the headrest with a processor based on biometric information of the occupant of the child safety seat; and
displaying a negative indicator on an output device when the position of the headrest is different from the specified position.

19. The method of claim 15, further comprising:
displaying a positive indicator on an output device upon the determining with the seat monitoring system that the position of the headrest satisfies specifications for the headrest.

20. The method of claim 15, wherein the tightening the belts of the harness includes tightening the belts with a motor.

21. The method of claim 15, wherein:
the seat monitoring system includes a processor;
the headrest position sensor includes a rotary sensor;
the headrest position sensor includes a tape coupled to the headrest and the rotary sensor;
the rotary sensor includes a spool;
the tape is wrapped around the spool of the rotary sensor; and
the measuring the position of the headrest includes determining with the processor a length of the tape unspooled from the spool of the rotary sensor.

22. A system, comprising:
a seat monitoring system configured to monitor status of a child safety seat;
wherein the seat monitoring system includes one or more sensors configured to sense the status of the child safety seat;
wherein the seat monitoring system includes an output device to provide the status of the child safety seat;
a processor being operatively connected to the sensors;

wherein the sensors include a headrest position sensor configured to determine position of a headrest of the child safety seat;
wherein the headrest position sensor is configured to send the position of the headrest to the processor;
wherein the processor is configured to compare the position of the headrest to a specified position;
wherein the processor is configured to determine the specified position for the headrest based on biometric information of an occupant of the child safety seat;
wherein the sensor includes an occupancy sensor configured to determine if the occupant is sitting in the child safety seat;
wherein the sensors include a buckle sensor configured to sense buckling status of a buckle of the child safety seat;
wherein the sensors include one or more tension sensors configured to sense tension of a harness of the child safety seat;
wherein the seat monitoring system includes a motor configured to adjust tension of the harness;
wherein the motor is configured to tighten the harness when the buckle is buckled and the occupancy sensor detects an occupant; and
wherein the motor is configured to tighten one or more belts of the harness until proper tension is reached.

23. The system of claim 22, wherein:
the headrest position sensor includes a rotary sensor;
the headrest position sensor includes a tape coupled to the headrest and the rotary sensor;
the rotary sensor includes a spool;
the tape is wrapped around the spool of the rotary sensor; and
a length of the tape unspooled from the spool corresponds to position of the headrest.

24. The system of claim 22, further comprising:
an output device configured to provide an alert when the headrest position sensor determines the headrest is in a proper position.

25. The system of claim 22, further comprising:
an input device configured to receive user inputs concerning the biometric information about the occupant of the child safety seat.

26. The system of claim 22, wherein the tension sensors include one or more strain gauges.

27. A system, comprising:
a seat monitoring system configured to monitor status of a child safety seat;
wherein the seat monitoring system includes one or more sensors configured to sense the status of the child safety seat;
wherein the seat monitoring system includes an output device to provide the status of the child safety seat;
a processor being operatively connected to the sensors;
wherein the sensors include a headrest position sensor configured to determine position of a headrest of the child safety seat;
wherein the headrest position sensor is configured to send the position of the headrest to the processor;
wherein the processor is configured to compare the position of the headrest to a specified position;
wherein the processor is configured to determine the specified position for the headrest based on biometric information of an occupant of the child safety seat; and
wherein the output device is configured to display a negative indicator when the position of the headrest is different from the specified position.

28. The system of claim 27, wherein:
the sensors include a buckle sensor configured to sense buckling status of a buckle of a harness of the child safety seat;
the sensors include one or more tension sensors configured to sense tension of the harness of the child safety seat; and
the seat monitoring system is configured to automatically adjust the tension of the harness based at least on tension data from the tension sensors.

* * * * *